(12) United States Patent
Chapoulaud et al.

(10) Patent No.: US 7,236,623 B2
(45) Date of Patent: Jun. 26, 2007

(54) ANALYTE RECOGNITION FOR URINALYSIS DIAGNOSTIC SYSTEM

(75) Inventors: Eric Chapoulaud, Pasadena, CA (US); Harvey L. Kasdan, Sherman Oaks, CA (US); Kenneth R. Castlemen, Friendswood, TX (US); Kenneth N. Good, Houston, TX (US)

(73) Assignee: International Remote Imaging Systems, Inc., Chatsworth, CA (US)

( * ) Notice: Subject to any disclaimer, the term of this patent is extended or adjusted under 35 U.S.C. 154(b) by 709 days.

(21) Appl. No.: 10/716,589

(22) Filed: Nov. 18, 2003

(65) Prior Publication Data

US 2004/0126008 A1 Jul. 1, 2004

Related U.S. Application Data

(63) Continuation-in-part of application No. 09/841,941, filed on Apr. 24, 2001, now Pat. No. 6,947,586.

(60) Provisional application No. 60/427,470, filed on Nov. 18, 2002, provisional application No. 60/199,237, filed on Apr. 24, 2000.

(51) Int. Cl.
*G06K 9/00* (2006.01)
(52) U.S. Cl. .................... 382/133; 382/190; 382/224
(58) Field of Classification Search .............. 382/133, 382/154–161, 203, 190, 225–226; 128/925
See application file for complete search history.

(56) References Cited

U.S. PATENT DOCUMENTS

| | | | |
|---|---|---|---|
| 4,180,798 A | 12/1979 | Komori et al. | |
| 4,338,024 A | 7/1982 | Bolz et al. | |
| 4,393,466 A | 7/1983 | Deindoerfer et al. | |
| 4,538,299 A | 8/1985 | DeForest | |
| 4,612,614 A | 9/1986 | Deindoerfer et al. | |
| 4,965,725 A * | 10/1990 | Rutenberg | 382/224 |
| 5,161,204 A * | 11/1992 | Hutcheson et al. | 382/157 |
| 5,218,646 A * | 6/1993 | Sirat et al. | 382/158 |
| 5,343,538 A | 8/1994 | Kasdan | |
| 5,436,978 A | 7/1995 | Kasdan | |
| 5,463,548 A | 10/1995 | Asada et al. | |

(Continued)

FOREIGN PATENT DOCUMENTS

WO    WO 91/02330    2/1991

OTHER PUBLICATIONS

Micheli-Tzanakou et al; "Neural Networks and Blood Cell Identification"; Journal of Medical Systems, vol. 21, No. 4, 1997.*

(Continued)

*Primary Examiner*—Joseph Mancuso
*Assistant Examiner*—Andrae Allison
(74) *Attorney, Agent, or Firm*—DLA Piper US LLP

(57) ABSTRACT

A method and apparatus for classifying a plurality of elements in images, where electronic images of a field of view containing elements are formed. Each of the elements has a plurality of features. A first subgroup of the plurality of features from the images of the plurality of elements are extracted and processed to segregate the plurality of elements into first and second groups. A classification class only for each of the elements in the first group is determined by selecting and processing a second subgroup of the extracted features to determine a physical characteristic of the element, and by selecting and processing a third subgroup of the extracted features in response to the determined physical characteristic to determine a classification class of the element. The second group of elements bypasses the determination of classification class.

30 Claims, 17 Drawing Sheets

U.S. PATENT DOCUMENTS

| | | | |
|---|---|---|---|
| 5,625,709 A | | 4/1997 | Kasdan |
| 5,703,959 A | * | 12/1997 | Asano et al. ............... 382/133 |
| 5,828,776 A | | 10/1998 | Lee et al. |
| 5,835,633 A | | 11/1998 | Fujisaki et al. |
| 5,889,892 A | | 3/1999 | Saito |
| 5,978,497 A | * | 11/1999 | Lee et al. ................... 382/133 |
| 5,987,158 A | | 11/1999 | Meyer et al. |
| 5,991,028 A | | 11/1999 | Cabib et al. |
| 6,091,843 A | * | 7/2000 | Horesh et al. .............. 382/133 |
| 6,246,785 B1 | | 6/2001 | Molnar et al. |
| 6,594,586 B1 | | 7/2003 | Song et al. |

OTHER PUBLICATIONS

Ercal et al; "Neural Network Diagnosis of Malignant From Color Images"; IEEE Transactions on Biomedical Engineering. vol. 41, No. 9, SEYIEMBER 1994.*

Parker, J.R. Algorithms For Image Processing And Computer Vision, John Wiley & Sons, Publishers, 1997, pp. 29-33, 69-102, 109, 165-171 and 176-219.

Mitra, Sanjit K., et al., Non-Linear Image Processing, Academic Press, 2000, Chapter 2, Part 2.4, pp. 49-53.

Errington, P.A. et al "Classification of Chromosomes Using A Combination Of Neural Networks," Proceedings of the International Conference on Neural Networks (ICNN), San Francisco, Mar. 28-Apr. 1, 1993, New York, IEEE, US, vol. 1, pp. 1236-1241.

NeuralWare, NeuralWorks Reference Guide: NeuralWorks Professional II/PLUS and NeuralWorks Explorer, Feb. 2000, pp. 17-19.

NeuralWare, Neural Computing: A Technology Handbook for NeuralWorks Professional II/PLUS and NeuralWorks Explorer, Feb. 2000, pp. 63-69 and 71-72.

* cited by examiner

FIG. 9A

| FEATURE NO. | HPF AMOR2 | PF ROUND/NOT ROUND | HPF ROUND4 | HPF NOT ROUND7 | LPF AMOR2 | LPF CAST/SGP/OTHER3 | LPF CAST3 | LPF OTHER4 |
|---|---|---|---|---|---|---|---|---|
| 0 | | | | | | | | |
| 1 | x | x | | | | | | |
| 2 | x | x | | | x | x | | |
| 3 | x | x | x | x | x | x | | x |
| 4 | x | x | | x | x | x | | x |
| 5 | | x | | | | x | | |
| 6 | x | x | | x | x | x | | |
| 7 | | x | | | | | | |
| 8 | | x | | | | | | |
| 9 | | x | | | | | | |
| 10 | | x | | x | x | | | |
| 11 | | x | x | | | | x | |
| 12 | | x | | x | x | | | |
| 13 | | x | x | | x | | | |
| 14 | | x | | x | x | | | |
| 15 | | x | x | x | | | | |
| 16 | | x | x | x | | x | | |
| 17 | | x | | | | x | | |
| 18 | x | x | | x | x | | | x |
| 19 | x | x | | x | x | x | x | x |
| 20 | | x | | x | x | x | x | x |
| 21 | x | x | | | x | | | x |
| 22 | x | x | | x | | | | |
| 23 | | x | | | x | x | x | x |
| 24 | | | | | | | | |
| 25 | | x | | | | | | |
| 26 | | x | | | | x | x | |
| 27 | | | | | | | | x |
| 28 | | | | | | | | |
| 29 | | x | | x | x | x | x | |
| 30 | | | | | | | | |
| 31 | | x | | | | | | |
| 32 | | x | | | | | | |
| 33 | | x | | | | | | |
| 34 | x | x | | x | | | | |
| 35 | | x | | x | x | | | x |
| 36 | | x | | | | | x | |
| 37 | x | x | | | x | | | x |
| 38 | | x | | | | | | |
| 39 | | x | | x | | | | |
| 40 | | x | | | | | | x |

FIG. 9B

| FEATURE NO. | HPF AMOR2 | PF ROUND/NOT ROUND | HPF ROUND4 | HPF NOT ROUND7 | LPF AMOR2 | LPF CAST/SQEP/OTHER3 | LPF CAST3 | LPF OTHER4 |
|---|---|---|---|---|---|---|---|---|
| 41 | | | | | | | | |
| 42 | x | x | | | | | | |
| 43 | | x | | | | | | x |
| 44 | | | | | | | | x |
| 45 | | | | x | | | | |
| 46 | x | | | | | | | x |
| 47 | x | | | x | | | | |
| 48 | x | | | | | x | | |
| 49 | | | | x | x | | | |
| 50 | | | | x | | | | |
| 51 | | | | | | | | |
| 52 | x | | | | | x | | |
| 53 | x | | | | | | x | |
| 54 | x | | | | | | | |
| 55 | x | | | x | | | | x |
| 56 | x | | | x | | | | x |
| 57 | x | | | x | | x | | |
| 58 | x | | | x | x | | | |
| 59 | | | | x | | | | x |
| 60 | | | | x | | | | |
| 61 | | | | | x | | x | |
| 62 | x | | | x | x | | | |
| 63 | x | | | x | x | | x | |
| 64 | | | | x | x | | | x |
| 65 | | | | x | | | | |
| 66 | | | x | x | x | x | | |
| 67 | | | | x | x | | | |
| 68 | x | | | | x | | | |
| 69 | | | | | x | | | |
| 70 | x | | | | x | | | |
| 71 | x | | | | x | | | |
| 72 | | | | x | x | | x | x |
| 73 | | | | x | | | | |
| 74 | | | | | | | | |
| 75 | x | | | | | | | |
| 76 | x | | x | x | x | | x | x |
| 77 | | | | x | | | | |
| 78 | | | | | x | | | |
| 79 | | | | | x | | | x |

FIG. 9C

| FEATURE NO. | HPF AMOR2 | PF ROUND/NOT ROUND | HPF ROUND4 | HPF NOT ROUND7 | LPF AMOR2 | LPF CAST2 | LPF CAST/SGEP/OTHER3 | LPF CAST3 | LPF OTHER4 |
|---|---|---|---|---|---|---|---|---|---|
| 80 |   |   |   |   |   |   |   |   |   |
| 81 | x |   |   |   |   |   |   |   |   |
| 82 | x |   | x | x | x |   | x | x | x |
| 83 | x |   | x | x |   |   | x | x | x |
| 84 | x |   |   | x | x |   | x |   | x |
| 85 |   |   |   |   |   |   |   |   |   |
| 86 | x |   |   | x |   |   |   |   |   |
| 87 | x |   |   | x | x |   | x | x | x |
| 88 |   |   |   | x |   |   | x | x | x |
| 89 |   |   | x | x | x |   |   |   |   |
| 90 |   |   | x | x |   |   |   |   |   |
| 91 |   |   |   |   |   |   |   |   |   |
| 92 | x |   | x | x | x |   | x | x | x |
| 93 |   |   | x | x | x |   | x | x | x |
| 94 |   |   |   | x |   |   |   |   | x |
| 95 |   |   |   |   |   |   |   |   |   |
| 96 | x |   |   |   |   |   |   |   |   |
| 97 | x |   |   | x | x |   | x |   |   |
| 98 |   |   |   | x |   |   | x |   |   |
| 99 |   |   |   |   |   |   |   |   |   |
| 100 |   |   |   | x |   |   |   |   |   |
| 101 |   |   |   | x |   |   |   |   |   |
| 102 | x |   |   |   | x |   |   |   |   |
| 103 |   |   |   | x |   |   | x |   |   |
| 104 | x |   |   | x | x |   |   |   |   |
| 105 |   |   |   | x |   |   |   |   |   |
| 106 | x |   |   | x |   |   |   |   |   |
| 107 |   |   |   | x |   |   | x |   |   |
| 108 | x |   |   | x |   |   |   |   |   |
| 109 |   |   |   |   |   |   |   |   | x |
| 110 |   |   |   |   |   |   | x |   |   |
| 111 |   |   |   |   |   |   |   |   |   |
| 112 | x |   |   |   |   |   |   |   |   |
| 113 |   |   |   |   |   |   |   | x |   |
| 114 |   |   |   |   |   |   |   |   |   |
| 115 | x |   |   |   |   |   |   |   |   |
| 116 |   |   |   |   |   |   |   |   |   |
| 117 |   |   |   | x | x |   |   |   |   |
| 118 |   |   |   | x |   |   |   | x |   |
| 119 |   |   |   |   |   |   |   |   |   |
| 120 |   |   |   |   |   |   |   |   |   |

FIG. 9D

| FEATURE NO. | HPF AMOR2 | PF ROUND/NOT ROUND | HPF ROUND4 | HPF NOT ROUND7 | LPF AMOR2 | LPF CAST/SQEP/OTHER3 | LPF CAST3 | LPF OTHER4 |
|---|---|---|---|---|---|---|---|---|
| 121 | | | | | | | | |
| 122 | | | | | | | | |
| 123 | | | | | | | | |
| 124 | | | | | | x | | |
| 125 | x | | | | | | x | |
| 126 | | | | | | | x | x |
| 127 | | | | x | | | | |
| 128 | | | | | x | | | |
| 129 | | | x | x | | | | |
| 130 | | | | x | | | | |
| 131 | | | | x | | | | |
| 132 | | | | | | | | |
| 133 | | | | | | | | |
| 134 | | | | | | | | |
| 135 | | | | x | | | | |
| 136 | | | | | | | | |
| 137 | | | | x | | | | |
| 138 | | | | | | | | |
| 139 | | | | | | | | |
| 140 | | | | x | | x | | |
| 141 | | | | x | | | | |
| 142 | x | | | x | | | | |
| 143 | x | | | x | | | | |
| 144 | | | x | | | | | |
| 145 | | | | x | | | | x |
| 146 | | | | x | | | | x |
| 147 | | | | x | | x | x | |
| 148 | | | x | x | | | x | x |
| 149 | | | | x | | | | x |
| 150 | | | | | | x | | x |
| 151 | | | x | | | x | | |
| 152 | | | | | | x | | |
| 153 | | | | | | | x | |
| 154 | | | | x | | | x | |
| 155 | | | | x | | | | |
| 156 | | | | | | | | |
| 157 | | | x | x | | x | x | x |
| 158 | | | | | | | | |
| 159 | | | | x | | | | |
| 160 | | | | | | | | |

FIG. 9E

| FEATURE NO | HPF AMOR2 | PF ROUND/NOT ROUND | HPF ROUND4 | HPF NOT ROUND7 | LPF AMOR2 | LPF CAST/SGEP/OTHER3 | LPF CAST3 | LPF OTHER4 |
|---|---|---|---|---|---|---|---|---|
| 161 | | | | | | | | |
| 162 | | | | | | | | |
| 163 | x | | | | | | | |
| 164 | | | | | | | | |
| 165 | | | | x | | | | |
| 166 | | | | x | | x | | |
| 167 | | | | x | | x | | |
| 168 | | | | | | | | x |
| 169 | | | | | | | | x |
| 170 | | | | x | | x | | |
| 171 | | | | x | | | | |
| 172 | | | | x | | | | |
| 173 | | | | | | | | |
| 174 | | | | | | | | |
| 175 | | | | | | x | x | |
| 176 | | | | x | | x | | |
| 177 | | | | x | | | | |
| 178 | | | | | | | | |
| 179 | | | | x | | | | |
| 180 | | | | x | | | | |
| 181 | x | | | | | | x | |
| 182 | x | | | | | | | |
| 183 | | | | | | | | |
| 184 | | | | | | | | |
| 185 | | | | | | | x | |
| 186 | | | | | | | | x |
| 187 | x | | | | | | | x |
| 188 | | | | | | | | x |
| 189 | | | | | | x | | |
| 190 | | | | | | | | x |
| 191 | | | | | | | x | |
| 192 | x | | | | | | | |
| 193 | | | | | | | | |
| 194 | | | | x | | | | |
| 195 | | | | | | | | |
| 196 | | | | | | | | |
| 197 | | | | | | | | |
| TOTAL: | 50 | 39 | 18 | 100 | 42 | 48 | 36 | 46 |

ANALYTE RECOGNITION FOR URINALYSIS DIAGNOSTIC SYSTEM

This application is a continuation-in-part of U.S. patent application Ser. No. 09/841,941, filed Apr. 24, 2001 now U.S. Pat. No. 6,947,586, which claims the benefit of U.S. Provisional Application No. 60/199,237, filed Apr. 24, 2000; and claims the benefit of U.S. Provisional Application No. 60/427,470, filed Nov. 18, 2002.

FIELD OF THE INVENTION

The present invention relates to an imaging apparatus having a plurality of neural nets, and a method of training the neural nets and a method of operating such an imaging apparatus. The apparatus can be used to detect and classify biological particles and more particularly, for detecting and classifying biological particles from human urine.

BACKGROUND OF THE INVENTION

Biological particle analysis apparatuses are well known in the art. See for example U.S. Pat. Nos. 4,338,024 and 4,393,466, which are assigned to the present assignee. Such prior art machines use a computer having a stored fixed program to detect and to classify detected biological particles.

Standard decision theory that is used to sort biological particle images is well known, and tends to sort particles by classification in a serial fashion. More specifically, for a urine sample containing a plurality of particle types, the particle images are searched for one or more particle features unique to a single particle type, and those images are extracted. This process is repeated for other particles one particle type at a time. The problem with this methodology is that each particle type can exhibit a range of values for the searched for particle feature(s), and the range of values can overlap with those of other particle types. There is also the problem of artifacts, which are particle images that have no clinical significance, e.g. talc or hair, or cannot be classified due to the sensitivity of the imaging device or other problems with the image (e.g. boundary of particle undefined due to partial capture). Artifact particle images need to be disregarded from the analysis in such a way as to not adversely affect the overall accuracy of the particle analysis. Thus, it can be difficult to accurately but reliably classify particles in a sample containing artifacts.

Most biological particle classification devices further necessitate manual manipulation to accurately classify the particles in the sample. While particle features can be used to segregate particle images by particle type, a trained user is needed to verify the result.

Neural net computers are also well known. The advantage of a neural net computer is its ability to "learn" from its experiences, and thus a neural net computer, in theory, can become more intelligent as it is trained.

There is a need for a biological particle classification method and apparatus for accurate and automated classification of biological particles in a sample, such as a urine sample.

SUMMARY OF THE INVENTION

In the present invention, a multi-neural net image detecting and classification apparatus is disclosed. The multi-neural net more efficiently uses the available information, which of necessity is finite, in that it more effectively partitions the decision space, thereby allowing this information to be used to make fewer decisions at each stage while still covering all outcomes with its totality of decisions. In addition, the neural net measures certainty at multiple stages of processing in order to force images to an abstention class, e.g. artifact. In some sense one can view this multi neural network as forcing the image data to run a gauntlet where at each stage of the gauntlet it is quite likely to be placed in an "I don't know" category. This is much more powerful than simply running through a single net because in essence what is accomplished is multiple fits of the data to templates which are much better defined than a single template could be because of the more effective use of the information.

The present invention also relates to a large set of particle features and a training method, which involves not simply a single pass through the training set, but selecting from a number of nets and then reducing the feature vector size. Finally, the present invention provides for preprocessing and post processing that enables heuristic information to be included as part of the decision making process. Post processing enables contextual information either available from other sources or gleaned from the actual decision making process to be used to further enhance the decisions.

In one aspect of the present invention, a method of classifying a plurality of elements in images includes forming electronic images of a field of view containing elements, wherein each of the elements has a plurality of features, extracting and processing a first subgroup of the plurality of features from the images of the plurality of elements to segregate the plurality of elements into first and second groups, and determining a classification class only for each of the elements in the first group by selecting and processing a second subgroup of the extracted features to determine a physical characteristic of the element, and selecting and processing a third subgroup of the extracted features in response to the determined physical characteristic to determine a classification class of the element, wherein the second group of elements bypasses the determination of classification class.

In another aspect of the present invention, an apparatus for classifying a plurality of elements in images includes an imaging system for forming electronic images of a field of view containing elements, wherein each of the elements has a plurality of features, and at least one processor for extracting and processing a first subgroup of the plurality of features from the images of the plurality of elements to segregate the plurality of elements into first and second groups, and determining a classification class only for each of the elements in the first group by selecting and processing a second subgroup of the extracted features to determine a physical characteristic of the element, and selecting and processing a third subgroup of the extracted features in response to the determined physical characteristic to determine a classification class of the element, wherein the second group of elements bypasses the determination of classification class.

Other objects and features of the present invention will become apparent by a review of the specification, claims and appended figures.

BRIEF DESCRIPTION OF DRAWINGS

FIGS. 9A to 9E are tables showing the particle features used with the various neural nets in the LPF and HPF scan processes of the present invention.

DETAILED DESCRIPTION OF THE PREFERRED EMBODIMENTS

The present invention comprises a method and apparatus for making decisions about the classification of individual particle images in an ensemble of images of biological particles for the purpose of identifying each individual image, and determining the number of images in each given class of particles.

Basic Method and Apparatus

Figure 1:
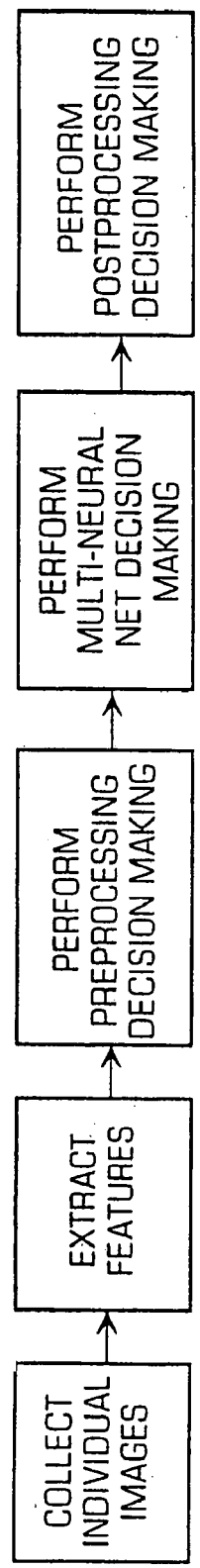
FIG. 1 is a flow diagram showing the method of the present invention.

The method is generally shown schematically in FIG. 1, and comprises 5 basic steps:

1) Collect individual images,
2) Extract particle features from each individual image,
3) Apply certain pre-processing rules to determine classifications of individual images or how the classification process will be performed,
4) Classify the individual images using a multiple neural net decision making structure, and
5) Analyze the ensemble of decisions or a subset of the ensemble of decisions to determine the overall classification of the ensemble or changes to classifications of certain subsets or individual images.

The method of the present invention further includes steps that train the individual neural nets used to make decisions, as well as steps that select the nets used in the final decision-making from among multiple nets produced by the training procedure.

Figure 2:
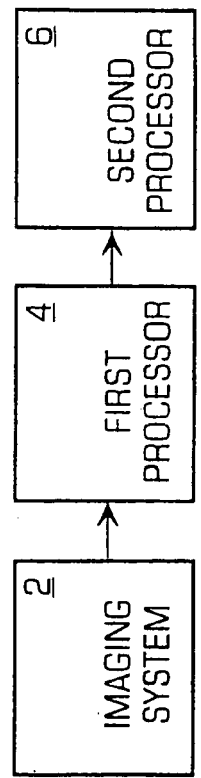
FIG. 2 is a schematic diagram of the apparatus of the present invention.

There are three major hardware elements that are used to implement the present invention: an imaging system 2, a first processor 4 and a second processor 6. These hardware elements are schematically illustrated in FIG. 2.

Imaging system 2 is used to produce images of fields of view of a sample containing the particles of interest. Imaging system 2 is preferably a well known flow microscope as described in U.S. Pat. Nos. 4,338,024, 4,393,466, 4,538,299 and 4,612,614, which are all hereby incorporated herein by reference. The flow microscope produces images of successive fields containing particles as they flow through a flow cell.

First processor 4 analyzes the images of successive fields, and isolates the particles in individual patches. A patch extraction apparatus (such as that described in U.S. Pat. Nos. 4,538,299 and 5,625,709, which are hereby incorporated herein by reference) is used to analyze the images produced by the imaging system and to define local areas (patches) containing particles of interest. The boundary of each particle is identified and defined, and used to extract the picture data for each particle from the larger field, thereby producing digital patch images that each contain the image of an individual particle of interest (resulting in a significant compression of the data subsequently required for processing). Imaging system 2 and first processor 4 combine to perform the first step (collection of individual images) shown in FIG. 1.

Second processor 6 analyzes each particle image to determine the classification of the particle image. Second processor 6 performs the last four steps shown in FIG. 1, as described below.

Boundary Enhancement—Mask Images

To enhance the particle feature extraction, the particle boundary is further refined, and black and white mask images of the particles are created. This process effectively changes all the digital image pixels outside the boundary of the particle (background pixels) to black pixels, and the pixels inside the particle boundary to white pixels. The resulting white images of the particles against a black background conveys the particles' shape and size very clearly, and are easy to operate on for particle features based on shape and size only (given that the pixels are either white or black).

Figure 3A:
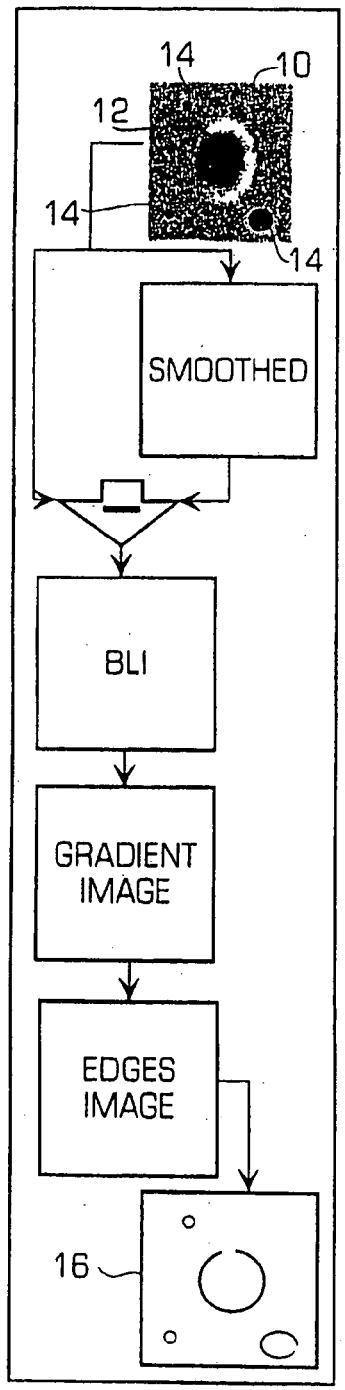
FIGS. 3A and 3B are flow diagrams illustrating the boundary enhancement of the present invention.
Figure 3B:
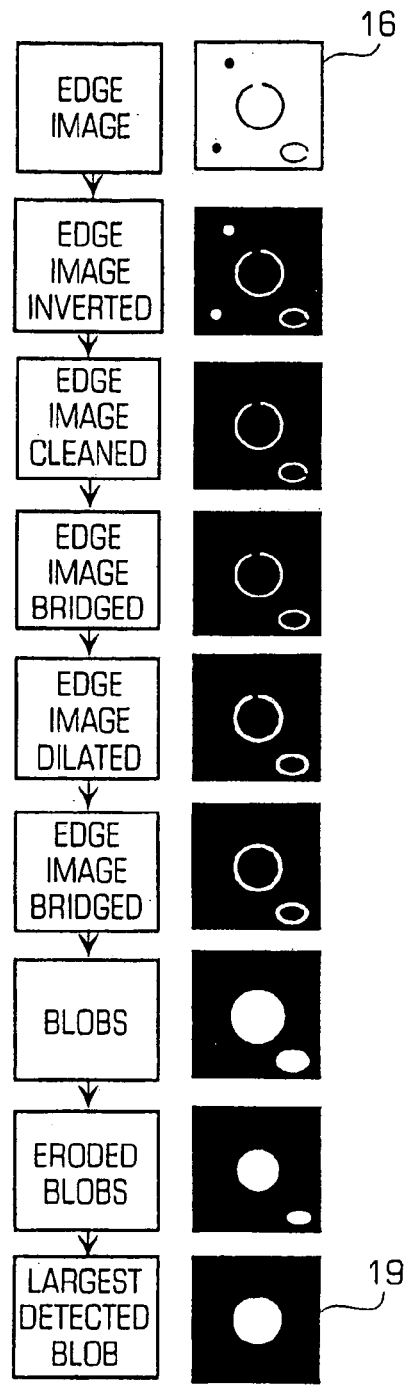

FIGS. 3A–3B illustrate the basic steps for transforming the particle image into a mask image. First, a Shen-Castan edge detector (as described in Parker, James R., *Algorithms for Image Processing and Computer Vision*, ISBN 0-471-14056-2, John Wiley & Sons, 1997, pp 29–32, and incorporated herein by reference) is used to define the edges of particles of interest, as illustrated in FIG. 3A. A particle image 10 typically contains images of particles of interest 12 and other particles 14. The particle image 10 is smoothed, and a band limited Laplacian image is created, followed by a gradient image. A threshold routine is used to detect the edges, whereby the locations where the intensity crosses a predetermined threshold are defined as edges. The detected edges are connected together to result in an edges image 16, which contains lines that correspond to detected boundaries that outline the various particles.

A mask image is created from the edge image 16 in the manner illustrated in FIG. 3B. The edge image 16 is inverted so the boundary lines are white and the background is black. Then, the image is cleaned of all small specks and particles too small to be of interest. Small gaps in the boundary lines are filled to connect some of the boundary lines together. The boundary lines are dilated to increase their width. This dilation is on the outer edges of the boundary lines, since the inner edges define the actual size of the particles. Disconnected pixels are bridged to create complete lines that enclose the particles. The inside of the boundaries are filled in to create blobs that represent the particles. The blobs are eroded to remove the pixels that had formed the boundary lines, so that the blobs have the correct size. Finally, the largest blob is detected, and all the remaining blobs are discarded. The resulting image is a mask image of the particle, where the white blob against the black background accurately corresponds to the size and shape of the particle of interest.

Particle Feature Extraction

Once the image of a particle of interest has been localized within a patch image, and its boundary further refined by creating a white mask image of the particle, the patch and mask images are further processed in order to extract particle features (feature data) from the particle image. Generally, the particle features numerically describe the size, shape, texture and color of the particles in numerous different ways that aid in the accurate classification of particle type. The particle features can be grouped in families that are related to one of these numerical descriptions, and can be extracted from the patch image, the mask image, or both.

The first family of particle features all relate to the shape of the particle, which aid in differentiating red and white blood cells which tend to be round, crystals which tend to be square or rectangular, and casts with tend to be elongated. The first family of particle features are:

1. Particle Area: the number of pixels contained within the particle boundary. Preferably, this particle feature is derived from the mask image of the particle.
2. Perimeter Length: the length of the particle boundary in pixels. Preferably, this is derived from the particle mask image by creating a 4-neighborhood perimeter image of the mask, and counting the number of non-zero pixels.
3. Shape Factor: an indication of the roundness of the particle. This is calculated as the square of the Perimeter Length, divided by the Particle Area.
4. Area to Perimeter Ratio: another indication of the roundness of the particle. This is calculated as the Particle Area divided by the Perimeter Length.

Figure 4:
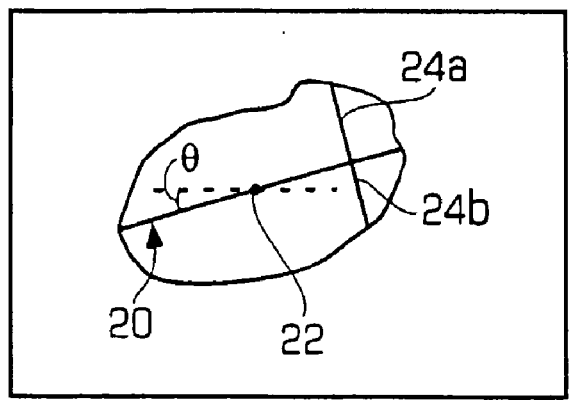
FIG. 4 is a diagram illustrating the symmetry feature extraction of the present invention.
Figure 5A:
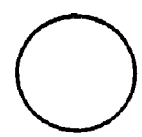
FIGS. 5A to 5D are drawings illustrating the skeletonization of various shapes.
Figure 5A:
Figure 5B:
Figure 5B:
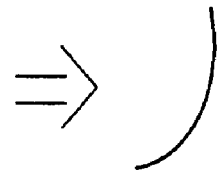
Figure 5C:
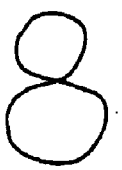
Figure 5C:
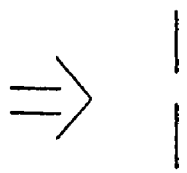
Figure 5D:
Figure 5D:
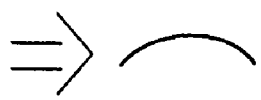

The second family of particle features relates to the symmetry of the particle, and in particular the determination of the number of lines of symmetry for any given shaped particle. This family of particle features are quite useful in distinguishing casts (typically having a line of symmetry along its long axis) and squamous epithelial cells (SQEPs, which generally have no line of symmetry). This family of particle features utilizes information derived from line segments applied at different angular orientations to the particle. As illustrated in FIG. 4, a line segment 20 is drawn through the centroid 22 of the mask image 19. For each point along the line segment 20, line segments 24a and 24b perpendicular thereto are drawn to extend away from the line segment 20 until they intersect the particle boundary, and the difference in length of the opposing perpendicular line segments 24a and 24b are calculated and stored. This calculation is repeated for each point along the line segment 20, where all the difference values are then summed and stored as a Symmetry Value for line segment 20. For a perfect circle, the Symmetry Value is zero for any line segment 20. The calculation of the Symmetry Value is then repeated for each angular rotation of line segment 20, resulting in a plurality of Symmetry Values, each one corresponding to a particular angular orientation of line segment 20. The Symmetry Values are then normalized by the Particle Area value, and sorted into an ordered list of Symmetry Values from low to high.

The second family of particle features are:
5. Minimum Symmetry: the lowest Symmetry Value in the ordered list, which represents the maximum symmetry exhibited by the particle at some value of rotation.
6. 20% Symmetry: the Symmetry Value that constitutes the $20^{th}$ percentile of the ordered list of Symmetry Values.
7. 50% Symmetry: the Symmetry Value that constitutes the $50^{th}$ percentile of the ordered list of Symmetry Values.
8. 80% Symmetry: the Symmetry Value that constitutes the $80^{th}$ percentile of the ordered list of Symmetry Values.
9. Maximum Symmetry: the highest Symmetry Value in the ordered list, which represents the minimum symmetry exhibited by the particle at some value of rotation.
10. Average Symmetry: the average value of the Symmetry Values.
11. Standard Deviation Symmetry: the standard deviation of the Symmetry Values.

The third family of particle features relate to skeletonization of the particle image, which produces one or more line segments that characterize both the size and the shape of the particle. These particle features are ideal in identifying analytes having multiple components in a cluster, such as budding yeast, hyphae yeast, and white blood cell clumps. These analytes will have skeletons with multiple branches, which are easy to differentiate from analytes having single branch skeletons. Creation of skeleton images is well known in the art of image processing, and is disclosed in Parker, James R., *Algorithms for Image Processing and Computer Vision*, ISBN 0-471-14056-2, John Wiley & Sons, 1997, pp 176–210), which is hereby incorporated herein by reference. Skeletonization essentially involves collapsing each portion of the particle boundary inwardly in a direction perpendicular to itself. For example, a perfect circle collapses to a single point; a crescent moon collapses to a curved line, a figure-8 collapses to 2 straight line segments, and a cell with an indentation collapses to a curved line, as illustrated in FIGS. 5A–5D respectively. The preferred embodiment utilizes two skeletonization algorithms: ZSH and BZS. ZSH is the Zhang-Suen thinning algorithm using Holt's variation plus staircase removal. BZS is the Zhang-Suen thinning algorithm using Holt's variation. FIG. 5.11 in *Parker* (p. 182) shows the difference between results when these algorithms are applied, along with C-code for each algorithm.

The third family of particle features are:
12. ZSH Skeleton Size: the size of the skeleton, preferably determined by counting the number of pixels forming the skeleton. The Skeleton Size for a perfect circle is 1, and for a crescent moon would be the length of the curved line.
13. ZSH Normalized Skeleton Size: Skeleton Size normalized by the size of the particle, determined by dividing Skeleton Size by Particle Area.
14. BZS Skeleton Size: the size of the skeleton, preferably determined by counting the number of pixels forming the skeleton. The Skeleton Size for a perfect circle is 1, and for a crescent moon would be the length of the curved line.
15. BZS Normalized Skeleton Size: Skeleton Size normalized by the size of the particle, determined by dividing Skeleton Size by Particle Area.

The fourth family of particle features relate to measuring the shape of the particle using radial lengths of radii that fit in the particle, and the quantile rankings of these values. Specifically, a centroid is defined inside the particle, preferably using the mask image, and a plurality of radii emanating from the centroid at different angles extend out to the particle boundary. The lengths of the radii are collected into a list of Radii Values, and the list is sorted from low to high values. A certain % quantile of an ordered list of values represents the value having a position in the list that corresponds to the certain percentage from the bottom of the list. For example, a 30% quantile of a list is the value that is positioned 30% up from bottom of the list, with 70% of the values being above it in the list. So, in an order list of 10 values, the 30% quantile value is the seventh value from the top of the list, and the 50% quantile is the median value of the list.

The fourth family of particle features are:
16. 25% Radii Value: the value corresponding to the 25% quantile of the list of Radii Values.
17. 50% Radii Value: the value corresponding to the 50% quantile of the list of Radii Values.
18. 75% Radii Value: the value corresponding to the 75% quantile of the list of Radii Values.
19. Smallest Mean Ratio: the ratio of the smallest Radii Value to the mean Radii Value.
20. Largest Mean Ratio: the ratio of the largest Radii Value to the mean Radii Value.
21. Average Radii Value: the average of the Radii Values.
22. Standard Deviation Radii Value: the standard deviation of the Radii Values.

The fifth family of particle features measures the intensity of the particle image. Light absorption properties of different analytes differ significantly. For example, crystals are generally refractive and may actually "concentrate" light so that their interior may be brighter than the background. Stained white blood cells, however, will typically be substantially darker than the background. The average intensity reveals the overall light absorbing quality of the particle, while the standard deviation of intensity measures the uniformity of the particle's absorbing quality. In order to measure intensity, the particle is preferably isolated by using the mask image in order to mask the patch image of the particle. Thus, the only pixels left (inside the mask) are those pixels contained inside the particle boundary. This family of particle features includes:
23. Average Pixel Value: the average pixel value for all the pixels inside the particle boundary.
24. Standard Deviation of Pixel Values: the standard deviation of pixel values for pixels inside the particle boundary.

The sixth family of particle features use the Fourier Transform of the particle to measure the radial distribution of the particle. The Fourier Transform depends on the size, shape and texture (i.e. fine grain structure) of the particle. In addition to adding texture, the Fourier Transform magnitude is independent of the position of the particle, and particle rotation is directly reflected as a rotation of the transform. Finding clusters of energy at one rotation is an indication of linear aspects of the particle (i.e. the particle has linear portions). This finding helps discriminate between particles such as crystals versus red blood cells. The Fourier Transform of the patch image of the particle is preferably calculated using a well known Fast Fourier Transform (FFT) algorithm with a window of 128×128 pixels. The following particle features are then calculated:
25. FFT Average Intensity of Rotated 128 Pixel Line: a queue listing of average pixel values along a 128 pixel line as a function of rotation angle. This is calculated by placing a radial line of length 128 pixels over the transform, and rotating the radial line through an arc of 180 degrees by increments of N degrees. For each increment of N degrees, the average of the pixel values along the radial line is calculated. The average pixel values for the N degree increments are stored in a queue as Average Intensity along with the corresponding angular increment.
26. FFT Maximum/Minimum 128 Pixel Angular Difference: the difference between the angular values that correspond to the highest and lowest Average Intensity values stored in the queue.
27. FFT 128 Pixel Average Intensity Standard Deviation: the standard deviation of the Average Intensity values stored in the queue.
28. FFT Average Intensity of Rotated 64 Pixel Line: same as the FFT Average Intensity of Rotated 128 Pixel Line, but instead using a 64 pixel length radial line.
29. FFT Maximum/Minimum 64 Pixel Angular Difference: same as the FFT Maximum/Minimum 128 Pixel Angular Difference, but instead using a 64 pixel length radial line.
30. FFT 64 Pixel Average Intensity Standard Deviation: same as the FFT 128 Pixel Average Intensity Standard Deviation, but instead using a 64 pixel length radial line.
31. FFT Average Intensity of Rotated 32 Pixel Line: same as the FFT Average Intensity of Rotated 128 Pixel Line, but instead using a 32 pixel length radial line.
32. FFT Maximum/Minimum 32 Pixel Angular Difference: same as the FFT Maximum/Minimum 128 Pixel Angular Difference, but instead using a 32 pixel length radial line.
33. FFT 32 Pixel Average Intensity Standard Deviation: same as the FFT 128 Pixel Average Intensity Standard Deviation, but instead using a 32 pixel length radial line.

Additional FFT particle features all related to standard deviation values based upon a rotated radial line of varying lengths are as follows:
34. FFT 128 Pixel Average Intensity Standard Deviation Sort: a sorted queue listing of the standard deviation of average pixel values along a 128 pixel line for different rotations. This is calculated by placing a radial line of length 128 pixels over the transform, and rotating the radial line through an arc of 180 degrees by increments of N degrees. For each increment of N degrees, the standard deviation value of the pixels on the line is calculated. The standard deviation values for all the N degree increments are sorted from low to high, and stored in a queue.
35. FFT 128 Pixel Minimum Radial Standard Deviation: the minimum radial standard deviation value retrieved from the sorted queue listing of standard deviation values.
36. FFT 128 Pixel Maximum Radial Standard Deviation: the maximum radial standard deviation value retrieved from the sorted queue listing of standard deviation values.
37. FFT 128 Pixel 25% Quantile Radial Standard Deviation: the radial standard deviation value from the queue corresponding to the 25% quantile of the values stored in the queue.
38. FFT 128 Pixel 50% Quantile Radial Standard Deviation: the radial standard deviation value from the queue corresponding to the 50% quantile of the values stored in the queue.
39. FFT 128 Pixel 75% Quantile Radial Standard Deviation: the radial standard deviation value from the queue corresponding to the 75% quantile of the values stored in the queue.
40. FFT 128 Pixel Minimum to Average Radial Standard Deviation Ratio: the ratio of the minimum to average radial standard deviation values stored in the queue.

41. FFT 128 Pixel Maximum to Average Radial Standard Deviation Ratio: the ratio of the maximum to average radial standard deviation values stored in the queue.
42. FFT 128 Pixel Average Radial Standard Deviation: the average radial standard deviation value of the values stored in the queue.
43. FFT 128 Pixel Standard Deviation of the Radial Standard Deviation: the standard deviation of all of the radial standard deviation values stored in the queue.
44. FFT 64 Pixel Average Intensity Standard Deviation Sort: the same as the FFT 128 Pixel Average Intensity Standard Deviation Sort, but instead using a 64 pixel length radial line.
45. FFT 64 Pixel Minimum Radial Standard Deviation: the same as the FFT 128 Pixel Minimum Radial Standard Deviation, but instead using a 64 pixel length radial line.
46. FFT 64 Pixel Maximum Radial Standard Deviation: the same as the FFT 128 Pixel Maximum Radial Standard Deviation, but instead using a 64 pixel length radial line.
47. FFT 64 Pixel 25% Quantile Radial Standard Deviation: the same as the FFT 128 Pixel 25% Quantile Radial Standard Deviation, but instead using a 64 pixel length radial line.
48. FFT 64 Pixel 50% Quantile Radial Standard Deviation: the same as the FFT 128 Pixel 50% Quantile Radial Standard Deviation, but instead using a 64 pixel length radial line.
49. FFT 64 Pixel 75% Quantile Radial Standard Deviation: the same as the FFT 128 Pixel 75% Quantile Radial Standard Deviation, but instead using a 64 pixel length radial line.
50. FFT 64 Pixel Minimum to Average Radial Standard Deviation Ratio: the same as the FFT 128 Pixel Minimum to Average Radial Standard Deviation Ratio, but instead using a 64 pixel length radial line.
51. FFT 64 Pixel Maximum to Average Radial Standard Deviation Ratio: the same as the FFT 128 Pixel Maximum to Average Radial Standard Deviation Ratio, but instead using a 64 pixel length radial line.
52. FFT 64 Pixel Average Radial Standard Deviation: the same as the FFT 128 Pixel Average Radial Standard Deviation, but instead using a 64 pixel length radial line.
53. FFT 64 Pixel Standard Deviation of the Radial Standard Deviation: the same as the FFT 128 Pixel Standard Deviation of the Radial Standard Deviation, but instead using a 64 pixel length radial line.
54. FFT 32 Pixel Average Intensity Standard Deviation Sort: the same as the FFT 128 Pixel Average Intensity Standard Deviation Sort, but instead using a 32 pixel length radial line.
55. FFT 32 Pixel Minimum Radial Standard Deviation: the same as the FFT 128 Pixel Minimum Radial Standard Deviation, but instead using a 32 pixel length radial line.
56. FFT 32 Pixel Maximum Radial Standard Deviation: the same as the FFT 128 Pixel Maximum Radial Standard Deviation, but instead using a 32 pixel length radial line.
57. FFT 32 Pixel 25% Quantile Radial Standard Deviation: the same as the FFT 128 Pixel 25% Quantile Radial Standard Deviation, but instead using a 32 pixel length radial line.
58. FFT 32 Pixel 50% Quantile Radial Standard Deviation: the same as the FFT 128 Pixel 50% Quantile Radial Standard Deviation, but instead using a 32 pixel length radial line.
59. FFT 32 Pixel 75% Quantile Radial Standard Deviation: the same as the FFT 128 Pixel 75% Quantile Radial Standard Deviation, but instead using a 32 pixel length radial line.
60. FFT 32 Pixel Minimum to Average Radial Standard Deviation Ratio: the same as the FFT 128 Pixel Minimum to Average Radial Standard Deviation Ratio, but instead using a 32 pixel length radial line.
61. FFT 32 Pixel Maximum to Average Radial Standard Deviation Ratio: the same as the FFT 128 Pixel Maximum to Average Radial Standard Deviation Ratio, but instead using a 32 pixel length radial line.
62. FFT 32 Pixel Average Radial Standard Deviation: the same as the FFT 128 Pixel Average Radial Standard Deviation, but instead using a 32 pixel length radial line.
63. FFT 32 Pixel Standard Deviation of the Radial Standard Deviation: the same as the FFT 128 Pixel Standard Deviation of the Radial Standard Deviation, but instead using a 32 pixel length radial line.

Even more FFT particle features are used, all related to average values based upon a rotated radial line of varying lengths:

64. FFT 128 Pixel Average Intensity Sort: a sorted queue listing of the average pixel values along a 128 pixel line for different rotations. This is calculated by placing a radial line of length 128 pixels over the transform, and rotating the radial line through an arc of 180 degrees by increments of N degrees. For each increment of N degrees, the average value of the pixels on the line is calculated. The average pixel values for all the N degree increments are sorted from low to high, and stored in a queue.
65. FFT 128 Pixel Minimum Average Value: the minimum radial average value retrieved from the sorted queue listing of average values.
66. FFT 128 Pixel Maximum Radial Value: the maximum radial average value retrieved from the sorted queue listing of average values.
67. FFT 128 Pixel 25% Quantile Radial Average Value: the radial average value from the queue corresponding to the 25% quantile of the average values stored in the queue.
68. FFT 128 Pixel 50% Quantile Radial Average Value: the radial average value from the queue corresponding to the 50% quantile of the average values stored in the queue.
69. FFT 128 Pixel 75% Quantile Radial Average Value: the radial average value from the queue corresponding to the 75% quantile of the average values stored in the queue.
70. FFT 128 Pixel Minimum to Average Radial Average Value Ratio: the ratio of the minimum to average radial average values stored in the queue.
71. FFT 128 Pixel Maximum to Average Radial Average Value Ratio: the ratio of the maximum to average radial average values stored in the queue.
72. FFT 128 Pixel Average Radial Standard Deviation: the average radial standard deviation value of the average values stored in the queue.
73. FFT 128 Pixel Standard Deviation of the Average Values: the standard deviation of all of the radial average values stored in the queue.

The seventh family of particle features use grayscale and color histogram quantiles of image intensities, which provide additional information about the intensity variation within the particle boundary. Specifically, grayscale, red, green and blue histogram quantiles provide intensity characterization in different spectral bands. Further, stains used with particle analysis cause some particles to absorb certain colors, such as green, while others exhibit refractive qualities at certain wavelengths. Thus, using all these particle features allows one to discriminate between a stained particle such as white blood cells that absorb the green, and crystals that refract yellow light.

Histograms, cumulative histograms and quantile calculations are disclosed in U.S. Pat. Nos. 4,538,299 and 5,343,538, which are hereby incorporated herein by reference. The particle image is typically captured using a CCD camera that breaks down the image into three color components. The preferred embodiment uses an RGB camera that separately captures the red, green and blue components of the particle image. The following particle features are calculated based upon the grayscale, red, green and blue components of the image:

74. Grayscale Pixel Intensities: a sorted queue listing of the grayscale pixel intensities inside the particle boundary. The grayscale value is a summation of the three color components. For each pixel inside the particle boundary (as masked by the mask image), the grayscale pixel value is added to a grayscale queue, which is then sorted (e.g. from low to high).
75. Minimum Grayscale Image Intensity: the minimum grayscale pixel value stored in the queue.
76. 25% Grayscale Intensity: the value corresponding to the 25% quantile of the grayscale pixel values stored in the queue.
77. 50% Grayscale Intensity: the value corresponding to the 50% quantile of the grayscale pixel values stored in the queue.
78. 75% Grayscale Intensity: the value corresponding to the 75% quantile of the grayscale pixel values stored in the queue.
79. Maximum Grayscale Image Intensity: the maximum grayscale pixel value stored in the queue.
80. Red Pixel Intensities: a sorted queue listing of the red pixel intensities inside the particle boundary. The particle image is converted so that only the red component of each pixel value remains. For each pixel inside the particle boundary (as masked by the mask image), the red pixel value is added to a red queue, which is then sorted from low to high.
81. Minimum Red Image Intensity: the minimum red pixel value stored in the queue.
82. 25% Red Intensity: the value corresponding to the 25% quantile of the red pixel values stored in the queue.
83. 50% Red Intensity: the value corresponding to the 50% quantile of the red pixel values stored in the queue.
84. 75% Red Intensity: the value corresponding to the 75% quantile of the red pixel values stored in the queue.
85. Maximum Red Image Intensity: the maximum red pixel value stored in the queue.
86. Green Pixel Intensities: a sorted queue listing of the green pixel intensities inside the particle boundary. The particle image is converted so that only the green component of the pixel value remains. For each pixel inside the particle boundary (as masked by the mask image), the green pixel value is added to a green queue, which is then sorted from low to high.
87. Minimum Green Image Intensity: the minimum green pixel value stored in the queue.
88. 25% Green Intensity: the value corresponding to the 25% quantile of the green pixel values stored in the queue.
89. 50% Green Intensity: the value corresponding to the 50% quantile of the green pixel values stored in the queue.
90. 75% Green Intensity: the value corresponding to the 75% quantile of the green pixel values stored in the queue.
91. Maximum Green Image Intensity: the maximum green pixel value stored in the queue.
92. Blue Pixel Intensities: a sorted queue listing of the blue pixel intensities inside the particle boundary. The particle image is converted so that only the blue component of the pixel value remains. For each pixel inside the particle boundary (as masked by the mask image), the blue pixel value is added to a blue queue, which is then sorted from low to high.
93. Minimum Blue Image Intensity: the minimum blue pixel value stored in the queue.
94. 25% Blue Intensity: the value corresponding to the 25% quantile of the blue pixel values stored in the queue.
95. 50% Blue Intensity: the value corresponding to the 50% quantile of the blue pixel values stored in the queue.
96. 75% Blue Intensity: the value corresponding to the 75% quantile of the blue pixel values stored in the queue.
97. Maximum Blue Image Intensity: the maximum blue pixel value stored in the queue.

The eighth family of particle features use concentric circles and annuli to further characterize the variation in the FFT magnitude distribution, which is affected by the size, shape and texture of the original analyte image. A center circle is defined over a centroid of the FFT, along with seven annuli (in the shape of a washer) of progressively increasing diameters outside of and concentric with the center circle. The first annulus has an inner diameter equal to the outer diameter of the center circle, and an outer diameter that is equal to the inner diameter of the second annulus, and so on. The following particle features are calculated from the center circle and seven annuli over the FFT:

98. Center Circle Mean Value: the mean value of the magnitude of the FFT inside the center circle.
99. Center Circle Standard Deviation: the standard deviation of the magnitude of the FFT inside the center circle.
100. Annulus to Center Circle Mean Value: the ratio of the mean value of the magnitude of the FFT inside the first annulus to that in the center circle.
101. Annulus to Center Circle Standard Deviation: the ratio of the standard deviation of the magnitude of the FFT inside the first annulus to that in the center circle.
102. Annulus to Circle Mean Value: the ratio of the mean value of the magnitude of the FFT inside the first annulus to that of a circle defined by the outer diameter of the annulus.
103. Annulus to Circle Standard Deviation: the ratio of the standard deviation of the magnitude of the FFT inside the first annulus to that of a circle defined by the outer diameter of the annulus.

104. Annulus to Annulus Mean Value: the ratio of the mean value of the magnitude of the FFT inside the first annulus to that of the annulus or center circle having the next smaller diameter (in the case of the first annulus, it would be the center circle).

105. Annulus to Annulus Standard Deviation: the ratio of the standard deviation of the magnitude of the FFT inside the first annulus to that of the annulus or center circle having the next smaller diameter (in the case of the first annulus, it would be the center circle).

106–111: Same as features 100–104, except the second annulus is used instead of the first annulus.

112–117: Same as features 100–104, except the third annulus is used instead of the first annulus.

118–123: Same as features 100–104, except the fourth annulus is used instead of the first annulus.

124–129: Same as features 100–104, except the fifth annulus is used instead of the first annulus.

130–135: Same as features 100–104, except the sixth annulus is used instead of the first annulus.

136–141: Same as features 100–104, except the seventh annulus is used instead of the first annulus.

154–197 is the same as 98–141, except they are applied to an FFT of the FFT of the particle image.

The last family of particle features use concentric squares with sides equal to 11%, 22%, 33%, 44%, 55%, and 66% of the FFT window size (e.g. 128) to further characterize the variation in the FFT magnitude distribution, which is affected by the size, shape and texture of the original analyte image. There are two well known texture analysis algorithms that characterize the texture of an FFT. The first is entitled Vector Dispersion, which involves fitting a planar to teach regions using normals, and is described on pages 165–168 of *Parker*, which is incorporated by reference. The second is entitled Surface Curvature Metric, which involves conforming a polynomial to the region, and is described on pages 168–171 of *Parker*, which is incorporated by reference. The following particle features are calculated from different sized windows over the FFT:

142–147: Application of the Vector Dispersion algorithm to the 11%, 22%, 33%, 44%, 55%, and 66% FFT windows, respectively.

148–153: Application of the Surface Curvature Metric algorithm to the 11%, 22%, 33%, 44%, 55%, and 66% FFT windows, respectively.

Processing and Decision Making

Once the foregoing particle features are computed, processing rules are applied to determine the classification of certain particles or how all of the particles in the ensemble from the sample will be treated. The preferred embodiment acquires the particle images using a low power objective lens (e.g. 10×) to perform low power field (LPF) scans with a larger field of view to capture larger particles, and a high power objective lens (e.g. 40×) to perform high power field (HPF) scans with greater sensitivity to capture the more minute details of smaller particles.

The system of the present invention utilizes separate multi neural net decision structures to classify particles captured in the LPF scan and HPF scan. Since most particles of interest will appear in one of the LPF or HPF scans, but not both, the separate decision structures minimize the number of particles of interest that each structure must classify.

Neural Net Structure

Figure 8:
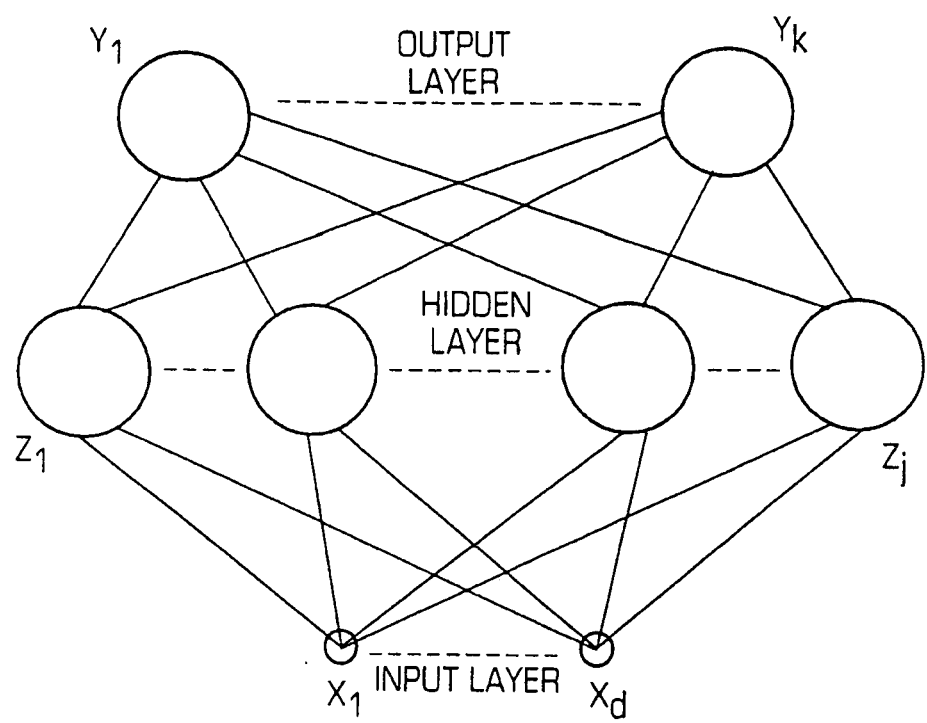
FIG. 8 is a schematic diagram of the neural net used with the present invention.

FIG. 8 illustrates the basic neural net structure used for all the neural nets in the LPF and HPF scans. The net includes an input layer with inputs $X_1$ to $X_d$, each corresponding to one of the particle features described above that are selected for use with the net. Each input is connected to each one of a plurality of neurons $Z_1$ to $Z_J$ in a hidden layer. Each of these hidden layer neurons $Z_1$ to $Z_J$ sums all the values received from the input layer in a weighted fashion, whereby the actual weight for each neuron is individually assignable. Each hidden layer neuron $Z_1$ to $Z_J$ also applies a non-linear function to the weighted sum. The output from each hidden layer neuron $Z_1$ to $Z_J$ is supplied each one of a second (output) layer of neurons $Y_1$ to $Y_K$. Each of the output layer neurons $Y_1$ to $Y_K$ also sums the inputs received from the hidden layer in a weighted fashion, and applies a non-linear function to the weighted sum. The output layer neurons provide the output of the net, and therefore the number of these output neurons corresponds to the number of decision classes that the net produces. The number of inputs equals the number of particle features that are chosen for input into the net.

As described later, each net is 'trained' to produce an accurate result. For each decision to be made, only those particle features that are appropriate to the decision of the net are selected for input into the net. The training procedure involves modifying the various weights for the neurons until a satisfactory result is achieved from the net as a whole. In the preferred embodiment, the various nets were trained using NeuralWorks, product version 5.30, which is produced by NeuralWare of Carnegie, Pa, and in particular the Extended Delta Bar Delta Back-propagation algorithm. The non-linear function used for all the neurons in all of the nets in the preferred embodiment is the hyperbolic tangent function, where the input range is constrained between –0.8 and +0.8 to avoid the low slope region.

LPF Scan Process

Figure 6A:
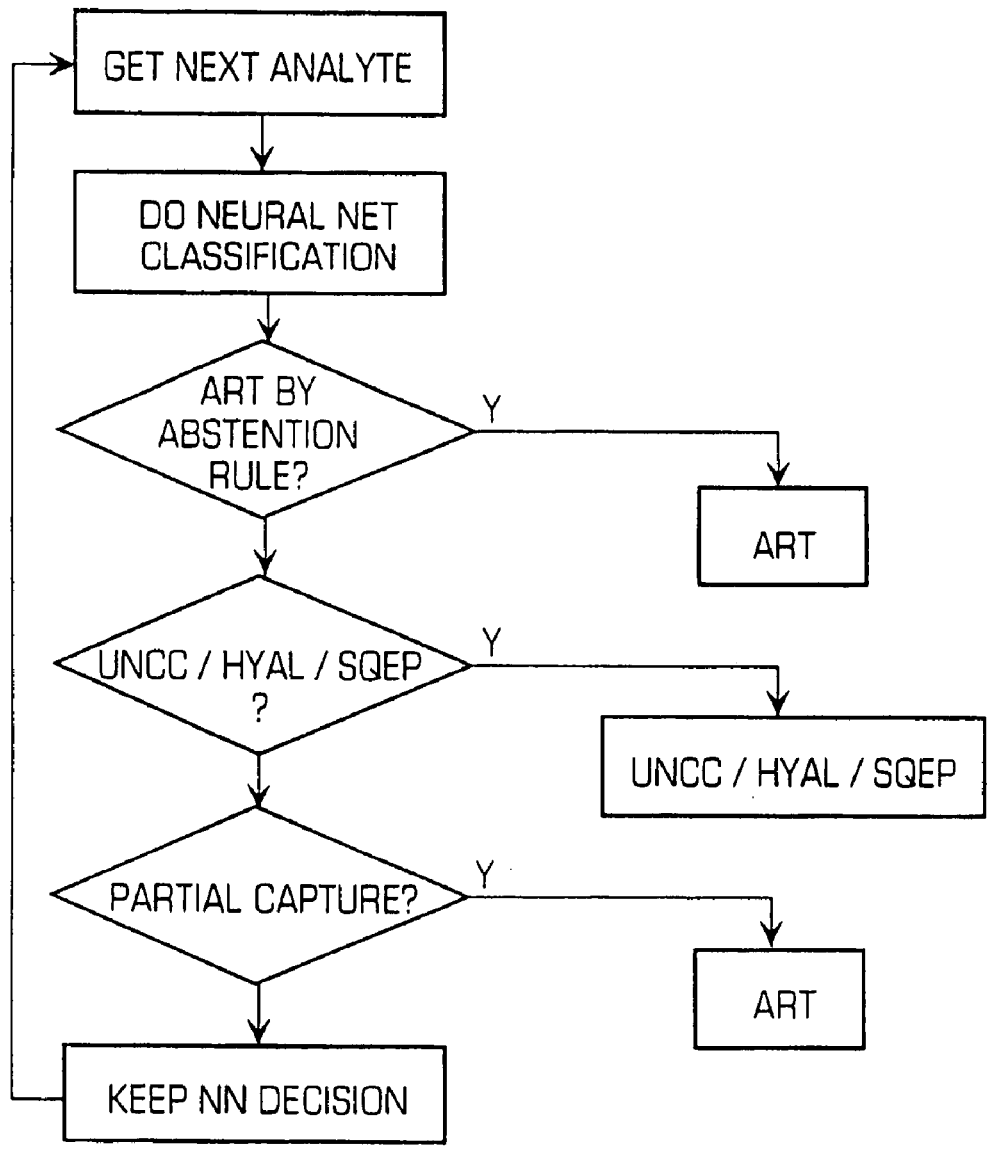
FIG. 6A is a flow diagram showing the LPF scan process of the present invention.
Figure 6B:
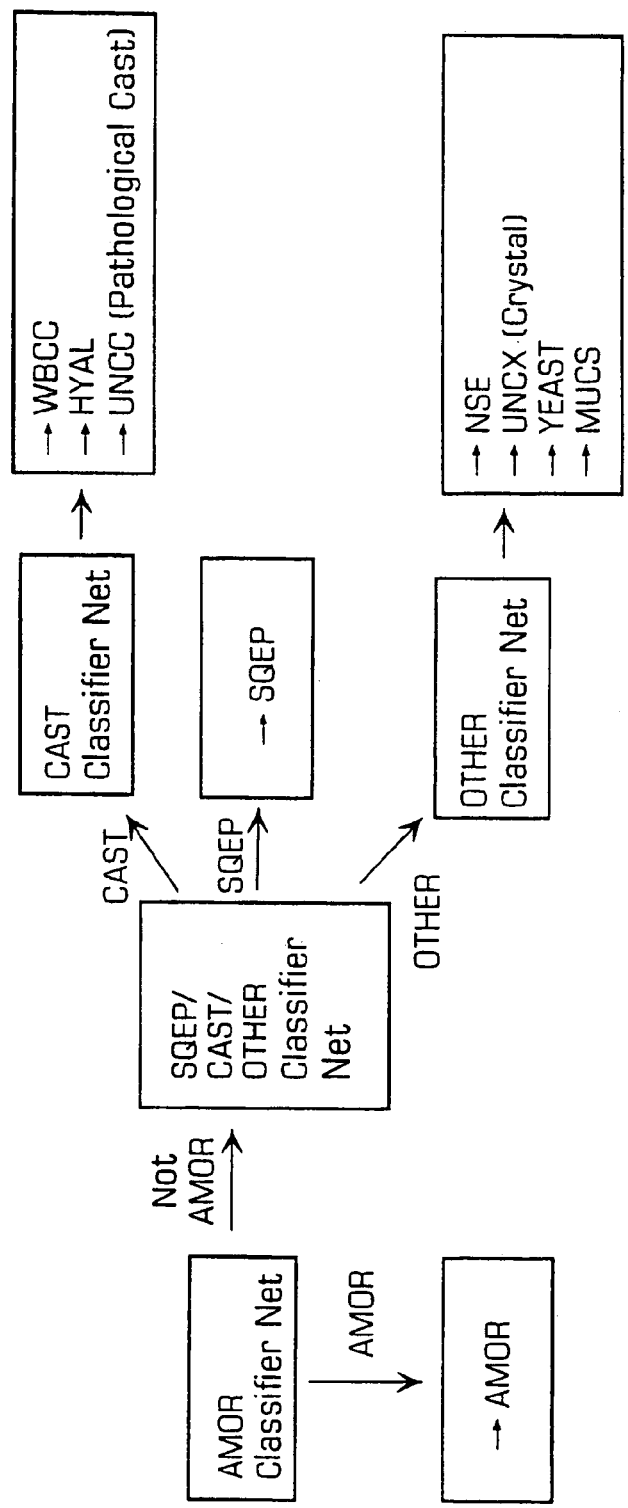
FIG. 6B is a flow diagram of the neural net classification used with the LPF scan process of the present invention.

The LPF scan process is illustrated in FIG. 6A, and starts by getting the next particle image (analyte) using the low power objective lens. A neural net classification is then performed, which involves the process of applying a cascading structure of neural nets to the analyte image, as illustrated in FIG. 6B. Each neural net takes a selected subgroup of the calculated 198 particle features discussed above, and calculates a classification probability factor ranging from zero to one that the particle meets the criteria of the net. The cascading configuration of the nets helps improve the accuracy of each neural net result downstream, because each net can be specifically designed for more accuracy given that the particle types it operates on have been prescreened to have or not have certain characteristics. For system efficiency, all 198 particle features are preferably calculated for each particle image, and then the neural net classification process of FIG. 6B is applied.

The first neural net applied to the particle image is the AMOR Classifier Net, which decides whether or not the particle is amorphous. For the preferred embodiment, this net includes 42 inputs for a selected subset of the 198 particle features described above, 20 neurons in the hidden layer, and two neurons in the output layer. The column entitled LPF AMOR2 in the table of FIGS. 9A–9E shows the numbers of the 42 particle features described above that were selected for use with this net. The first and second outputs of this net correspond to the probabilities that the particle is or is not amorphous, respectively. Whichever probability is higher constitutes the decision of the net. If the net decides the particle is amorphous, then the analysis of the particle ends.

If it is decided that the particle is not amorphous, then the SQEP/CAST/OTHER Classifier Net is applied, which decides whether the particle is a Squamous Epithelial cell (SQEP), a Cast cell (CAST), or another type of cell. For the preferred embodiment, this net includes 48 inputs for a selected subset of the 198 particle features described above, 20 neurons in the hidden layer, and three neurons in the output layer. The column entitled LPF CAST/SQEP/OTHER3 in the table of FIGS. 9A–9C shows the numbers of the 48 particle features described above that were selected for use with this net. The first, second and third outputs of this net correspond to the probabilities that the particle a Cast, a SQEP, or another particle type, respectively. Whichever probability is highest constitutes the decision of the net.

If it is decided that the particle is a Cast cell, then the CAST Classifier Net is applied, which decides whether the particle is a White Blood Cell Clump (WBCC), a Hyaline Cast Cell (HYAL), or an unclassified cast (UNCC) such as a pathological cast cell. For the preferred embodiment, this net includes 36 inputs for a selected subset of the 198 particle features described above, 10 neurons in the hidden layer, and three neurons in the output layer. The column entitled LPF CAST3 in the table of FIGS. 9A–9E shows the numbers of the 36 particle features described above that were selected for use with this net. The first, second and third outputs of this net correspond to the probabilities that the particle is a WBCC, HYAL or UNCC. Whichever probability is highest constitutes the decision of the net.

If it is decided that the particle is a Squamous Epithelial cell, then the decision is left alone.

If it is decided that the particle is another type of cell, then the OTHER Classifier Net is applied, which decides whether the particle is a Non-Squamous Epithelial cell (NSE) such as a Renal Epithelial cell or a transitional Epithelial cell, an Unclassified Crystal (UNCX), Yeast (YEAST), or Mucus (MUCS). For the preferred embodiment, this net includes 46 inputs for a selected subset of the 198 particle features described above, 20 neurons in the hidden layer, and four neurons in the output layer. The column entitled LPF OTHER4 in the table of FIGS. 9A–9E shows the numbers of the 46 particle features described above that were selected for use with this net. The first, second, third and fourth outputs of this net correspond to the probabilities that the particle is a NSE, UNCX, YEAST, or MUCS. Whichever probability is highest constitutes the decision of the net.

Referring back to FIG. 6A, once the Neural Net Classification has decided the particle type, an ART by Abstention Rule is applied, to determine if the particle should be classified as an artifact because none of the nets gave a high enough classification probability factor to warrant a particle classification. The ART by Abstention Rule applied by the preferred embodiment is as follows: if the final classification by the net structure is HYAL, and the CAST probability was less than 0.98 at the SQEP/CAST/Other net, then the particle is reclassified as an artifact. Also, if the final classification by the net structure was a UNCC, and the CAST probability was less then 0.95 at the SQEP/CAST/Other net, then the particle is reclassified as an artifact.

The next step shown in FIG. 6A applies to particles surviving the ART by Abstention Rule. If the particle was classified by the net structure as a UNCC, a HYAL or a SQEP, then that classification is accepted unconditionally. If the particle was classified as another type of particle, then a partial capture test is applied to determine if the particle should be classified as an artifact. Partial capture test determines if the particle boundary hits one or more particle image patch boundaries, and thus only part of the particle image was captured by the patch image. The partial capture test of the preferred embodiment basically looks at the pixels forming the boundary of the patch to ensure they represent background pixels. This is done by collecting a cumulative intensity histogram on the patch boundaries, and calculating Lower and Upper limits of these intensities. The Lower limit in the preferred embodiment is either the third value from the bottom of the histogram, or the value 2% from the bottom of the histogram, whichever is greater. The Upper limit is either the third value from the top of the histogram, or the value 2% from the top of the histogram, whichever is greater. The patch image is deemed a partial capture if the lower limit is less than 185 (e.g. of a pixel intensity that ranges from 0 to 255). The patch is also deemed a partial capture if the upper limit is less than or equal to 250 and the lower limit is less than 200 (this is to take care of the case where the halo of a particle image touches the patch image boundary). All particles surviving the partial capture test maintain their classification, and the LPF scan process is complete.

In the preferred embodiment, the partial capture test is also used as one of the particle features used by some of the neural nets. The feature value is 1 if the particle boundary is found to hit one or more particle image patch boundaries, and a zero if not. This particle feature is numbered "0" in FIGS. 9A–9E.

HPF Scan Process

Figure 7A:
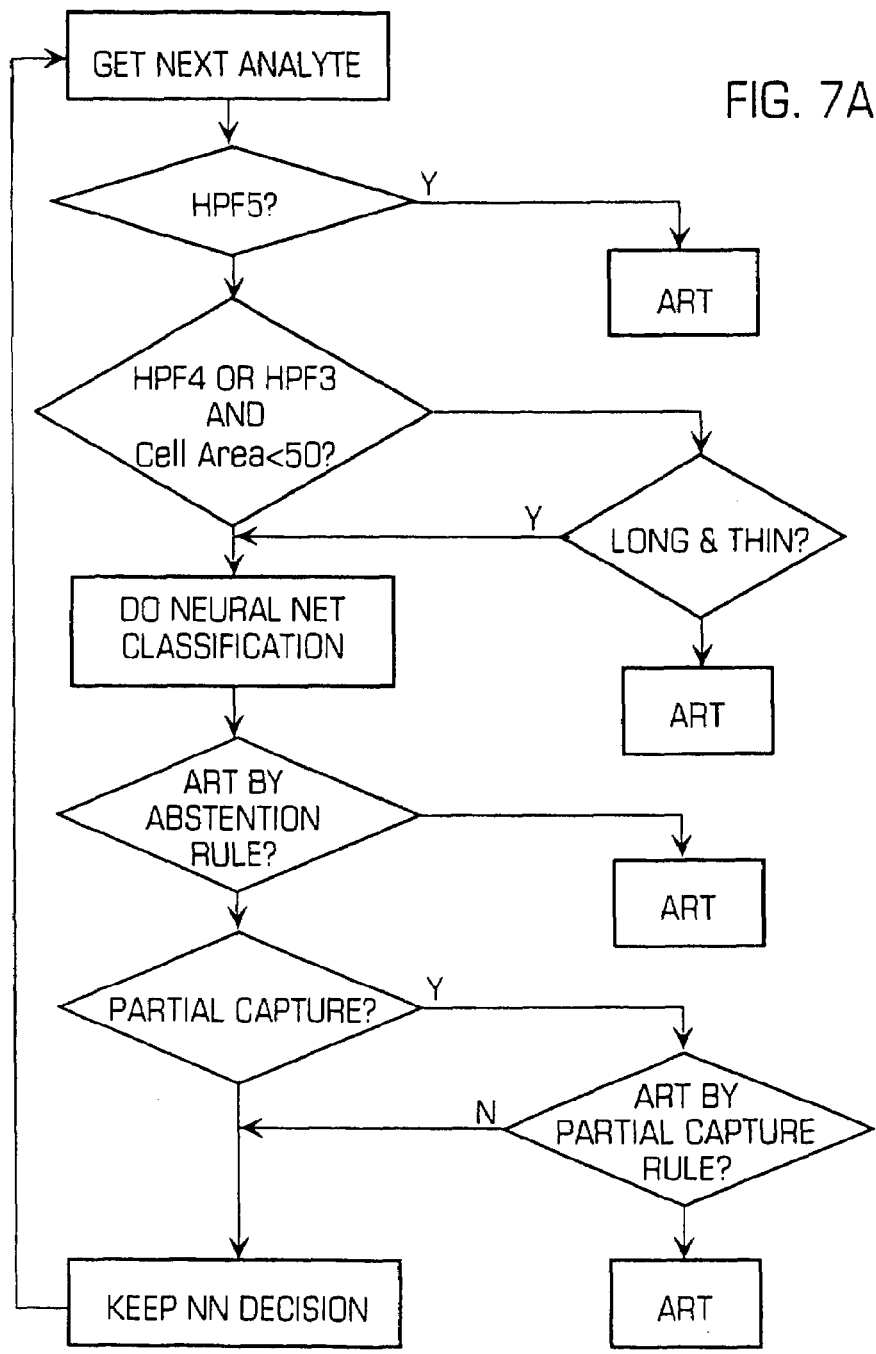
FIG. 7A is a flow diagram showing the HPF scan process of the present invention.

The HPF scan process is illustrated in FIG. 7A, and starts by getting the next particle image (analyte) using the high power objective lens. Two pre-processing artifact classification steps are performed before submitting the particles to neural net classification. The first preprocessing step begins by defining five size boxes (HPF1–HPF5), with each of the particles being associated with the smallest box that it can completely fit in to. In the preferred embodiment, the smallest box HPF5 is 12 by 12 pixels, and the largest box HPF1 is 50 by 50 pixels. All particles associated with the HPF5 box are classified as an artifact and removed from further consideration, because those particles are too small for accurate classification given the resolution of the system.

The second pre-processing step finds all remaining particles that are associated with the HPF3 or HPF4 boxes, that have a cell area that is less than 50 square pixels, and that are not long and thin, and classifies them as artifacts. This second preprocessing step combines size and aspect ratio criteria, which eliminates those smaller particles which tend to be round. Once particles associated with the HPF3 or HPF4 boxes and with a cell area under 50 square pixels have been segregated, each such particle is classified as an artifact if either of the following two criteria are met. First, if the square of the particle perimeter divided by the particle area is less than 20, then the particle is not long and thin and is classified an artifact. Second, if the ratio of eigenvalues of the covariance matrix of X and Y moments (which is also called the Stretch Value) is less than 20, then the particle is not long and thin and is classified an artifact.

Figure 7B:
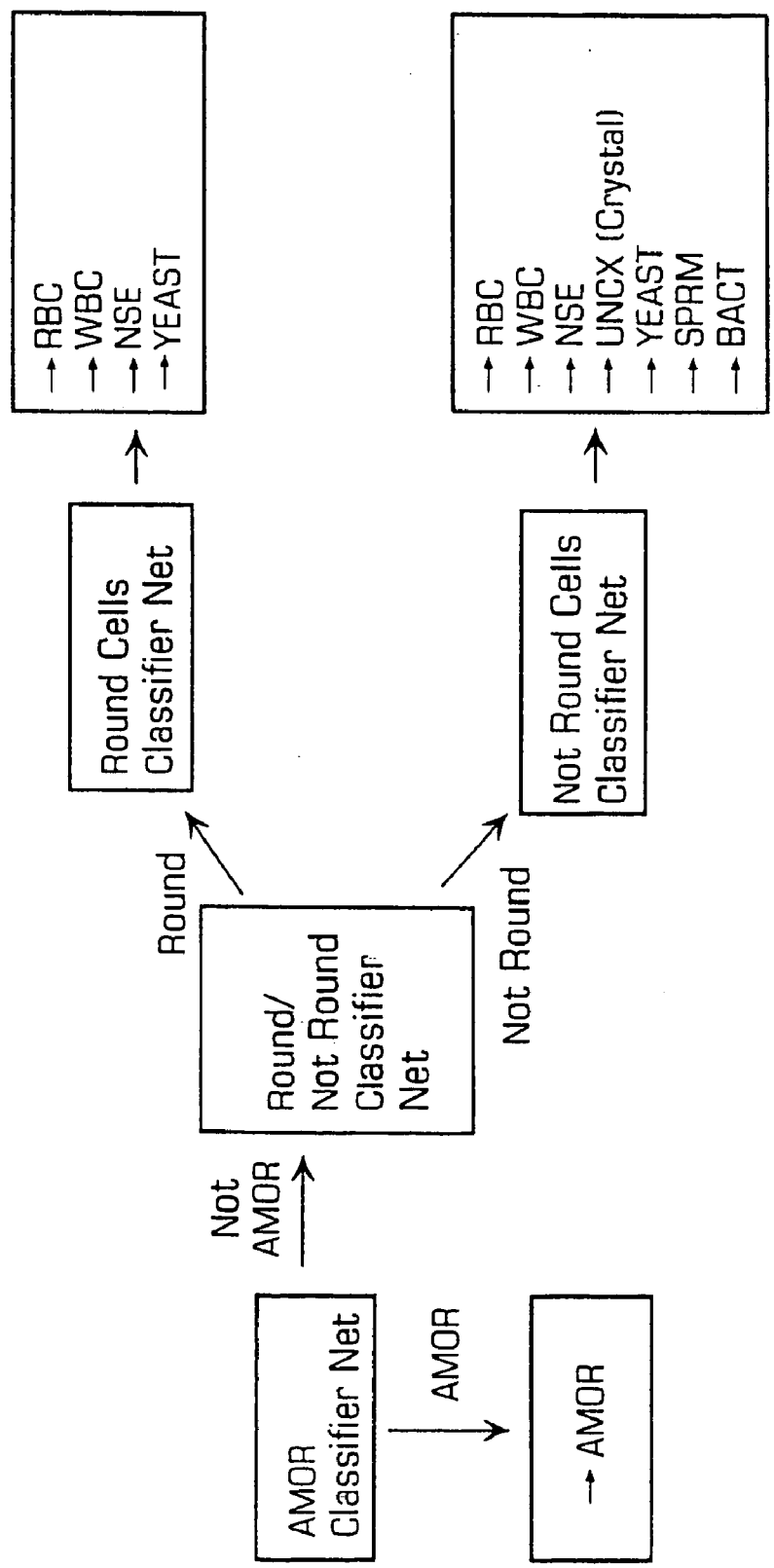
FIG. 7B is a flow diagram of the neural net classification used with the HPF scan process of the present invention.

Particle images that survive the two preprocessing steps described above are subjected to the cascading structure of neural nets illustrated in FIG. 7B. Each neural net takes a selected subgroup of the calculated 198 particle features discussed above, and calculates a classification probability factor ranging from zero to one that the particle meets the criteria of net. As with the cascading configuration of the nets, this helps improve the accuracy of each neural net result downstream, and preferably all 198 particle features are calculated for each particle image before the HPF scan commences.

The first neural net applied to the particle image is the AMOR Classifier Net, which decides whether or not the particle is amorphous. For the preferred embodiment, this net includes 50 inputs for a selected subset of the 198 particle features described above, 10 neurons in the hidden layer, and two neurons in the output layer. The column entitled HPF AMOR2 in the table of FIGS. 9A–9E shows the numbers of the 50 particle features described above that were selected for use with this net. The first and second outputs of this net correspond to the probabilities that the particle is or is not amorphous. Whichever probability is higher constitutes the decision of the net. If the net decides the particle is amorphous, then the analysis of the particle ends.

If it is decided that the particle is not amorphous, then the Round/Not Round Classifier Net is applied, which decides whether the particle shape exhibits a predetermined amount of roundness. For the preferred embodiment, this net includes 39 inputs for a selected subset of the 198 particle features described above, 20 neurons in the hidden layer, and two neurons in the output layer. The column entitled HPF ROUND/NOT ROUND2 in the table of FIGS. 9A–9E shows the numbers of the 39 particle features described above that were selected for use with this net. The first and second outputs of this net correspond to the probabilities that the particle is or is not 'round'. Whichever probability is highest constitutes the decision of the net.

If it is decided that the particle is 'round', then the Round Cells Classifier Net is applied, which decides whether the particle is a Red Blood Cell (RBC), a White Blood Cell (WBC), a Non-Squamous Epithelial cell (NSE) such as a Renal Epithelial cell or a transitional Epithelial cell, or Yeast (YEAST). For the preferred embodiment, this net includes 18 inputs for a selected subset of the 198 particle features described above, 3 neurons in the hidden layer, and three neurons in the output layer. The column entitled HPF Round4 in the table of FIGS. 9A–9E shows the numbers of the 18 particle features described above that were selected for use with this net. The first, second, third and fourth outputs of this net correspond to the probabilities that the particle is a RBC, a WBC, a NSE or YEAST, respectively. Whichever probability is highest constitutes the decision of the net.

If it is decided that the particle is not 'round', then the Not Round Cells Classifier Net is applied, which decides whether the particle is a Red Blood Cell (RBC), a White Blood Cell (WBC), a Non-Squamous Epithelial cell (NSE) such as a Renal Epithelial cell or a transitional Epithelial cell, an Unclassified Crystal (UNCX), Yeast (YEAST), Sperm (SPRM) or Bacteria (BACT). For the preferred embodiment, this net includes 100 inputs for a selected subset of the 198 particle features described above, 20 neurons in the hidden layer, and seven neurons in the output layer. The column entitled HPF NOT ROUND7 in the table of FIGS. 9A–9E shows the numbers of the 100 particle features described above that were selected for use with this net. The seven outputs of this net correspond to the probabilities that the particle is a RBC, a WBC, a NSE, a UNCX, a YEAST, a SPRM or a BACT. Whichever probability is highest constitutes the decision of the net.

Referring back to FIG. 7A, once the Neural Net Classification has decided the particle type, an ART by Abstention Rule is applied, to determine if the particle should be classified as an artifact because none of the nets gave a high enough classification probability factor to warrant a particle classification. The ART by Abstention Rule applied by the preferred embodiment reclassifies four types of particles as artifacts if certain criteria are met. First, if the final classification by the net structure is Yeast, and the YEAST probability was less than 0.9 at the Not Round Cells Classification Net, then the particle is reclassified as an artifact.

Second, if the final classification by the net structure was a NSE, and the NSE probability was less than 0.9 at the Round Cells Classifier Net, or the round probability was less than 0.9 at the Round/Not Round Classifier Net, then the particle is reclassified as an artifact. Third, if the final classification by the net structure was a not round NSE, and the NSE probability was less than 0.9 at the Not Round Cells Classifier Net, then the particle is reclassified as an artifact. Fourth, if the final classification by the net structure was a UNCX, and the UNCX probability was less than 0.9 at the Not Round Cells Classifier Net, or the round probability was less than 0.9 at the Round/Not Round Classifier Net, then the particle is reclassified as an artifact.

The next step shown in FIG. 7A is a partial capture test, which is applied to all particles surviving the ART by Abstention Rule. The partial capture test determines if the particle should be classified as an artifact because the particle boundary hits one or more particle image patch boundaries, and thus only part of the particle image was captured by the patch image. As with the LPF scan, the partial capture test of the preferred embodiment basically looks at the pixels forming the boundary of the patch to ensure they represent background pixels. This is done by collecting a cumulative intensity histogram on the patch boundaries, and calculating lower and upper limits of these intensities. The lower limit in the preferred embodiment is either the third value from the bottom of the histogram, or the value 2% from the bottom of the histogram, whichever is greater. The upper limit is either the third value from the top of the histogram, or the value 2% from the top of the histogram, whichever is greater. The patch image is deemed a partial capture if the lower limit is less than 185 (e.g. of a pixel intensity that ranges from 0 to 255). The patch is also deemed a partial capture if the upper limit is less than or equal to 250 and the lower limit is less than 200 to take care of the case where the halo of a particle image touches the patch image boundary.

All particles surviving the partial capture test maintain their classification. All particles deemed a partial capture are further subjected to an ART by Partial Capture Rule, which reclassifies such particles as an artifact if any of the following 6 criteria are met:

1. If it was associated with the HPF1 size box.
2. If it was not classified as either a RBC, WBC, BYST, OR UNCX.
3. If it was classified as a RBC, and if it was associated with the HPF2 size box or had a Stretch Value greater than or equal to 5.0.
4. If it was classified as a WBC, and had a Stretch Value greater than or equal to 5.0.
5. If it was classified as a UNCX, and had a Stretch Value greater than or equal to 10.0.
6. If it was classified as a BYST, and had a Stretch Value greater than or equal to 20.0.

If none of these six criteria are met by the particle image, then the neural net classification is allowed to stand even though the particle was deemed a partial capture, and the HPF scan process is complete. These six rules were selected to keep particle classification decisions in cases where partial capture does not distort the neural net decision making process, while eliminating those particles where a partial capture would likely lead to an incorrect decision.

To best determine which features should be used for each of the neural nets described above, the feature values input to any given neural net are modified one at a time by a small amount, and the effect on the neural net output is recorded. Those features having the greatest affect on the output of the neural net should be used.

Post Processing Decision Making

Once all the particles images are classified by particle type, post decision processing is performed to further increase the accuracy of the classification results. This processing considers the complete set of results, and removes classification results that as a whole are not considered trustworthy.

User settable concentration thresholds are one type of post decision processing that establishes a noise level threshold for the overall results. These thresholds are settable by the user. If the neural net classified image concentration is lower than the threshold, then all the particles in the category are reclassified as artifacts. For example, if the HPF scan finds only a few RBC's in the entire sample, it is likely these are erroneous results, and these particles are reclassified as artifacts.

Excessive amorphous detection is another post decision process that discards questionable results if too many particles are classified as amorphous. In the preferred embodiment, if there are more than 10 non-amorphous HPF patches, and more than 60% of them are classified to be amorphous by the neural nets, then the results for the entire specimen are discarded as unreliable.

The preferred embodiment also includes a number of LPF false positive filters, which discard results that are contradictory or questionable. Unlike HPF particles, LPF artifacts come in all shapes and sizes. In many cases, given the resolution of the system, it is impossible to distinguish LPF artifacts from true clinically significant analytes. In order to reduce false positives due to LPF artifacts, a number of filters are used to look at the aggregate decisions made by the nets, and discard those results that simply make no sense. For example, if the HPF WBC count is less than 9, then all LPF WBCC's should be reclassified as artifacts, since clumps of white blood cells are probably not present if white blood cells are not found in significant numbers. Further, the detection of just a few particles of certain types should be disregarded, since it is unlikely that these particles are present in such low numbers. In the preferred embodiment, the system must find more than 3 LPF UNCX detected particles, or more than 2 LPF NSE detected particles, or more than 3 LPF MUC detected particles, or more than 2 HPF SPRM detected particles, or more than 3 LPF YEAST detected particles. If these thresholds are not met, then the respective particles are re-classified as artifacts. Moreover, there must be at least 2 HPF BYST detected particles to accept any LPF YEAST detected particles.

Neural Net Training and Selection

Each neural net is trained using a training set of pre-classified images. In addition to the training set, a second smaller set of pre-classified images is reserved as the test set. In the preferred embodiment, the commercial program NeuralWare, published by NeuralWorks, is used to perform the training. Training stops when the average error on the test set is minimized.

This process is repeated for multiple starting seeds and net structures (i.e. number of hidden layers and elements in each layer). The final choice is based not only on the overall average error rate, but also to satisfy constraints on errors between specific classes. For example, it is undesirable to identify a squamous epithelial cell as a pathological cast because squamous epithelial cells occur normally in female urine specimens, but pathological casts would indicate an abnormal situation. Therefore, the preferred embodiment favors nets with SQEP to UNCC error rates less than 0.03 at the expense of a greater misclassification rate of UNCC as SQEP. This situation somewhat decreases the sensitivity to UNCC detection, but minimizes false positives in female specimens, which with sufficiently high rate of occurrence would render the system useless since a high proportion of female urine samples would be called abnormal. Thus, it is preferable to employ a method that not only minimizes the overall error rate, but also considers the cost of specific error rates in the selection of the "optimal" nets, and build this selection criterion into the net training.

As can be seen from the forgoing, the method and apparatus of the present invention differs from the prior art in the following respect. In the prior art, at each stage of processing, a classification of a particle is made, with the remaining unclassified particles considered artifacts or unknowns. In order to minimize the classification of particles as artifacts or unknowns, the range of values for classification at each stage is large. This can cause misclassification of particles.

In contrast, the range of values for classification at each stage of the present invention is narrow, resulting in only particles having greater probability of certainty being so classified, and the remainder being classified in a classification for further processing that is related to the previous stage of processing. The multi-net structure of the present invention utilizes subgroups of the particle features to partition the decision space by an attribute or physical characteristic of the particle (e.g. its roundness) and/or by individual and group particle classification that includes an unknown category. This partitioned decision space, which produces probability factors at each decision, more efficiently uses the available information, which of necessity is finite, and effectively allows this information to be used to make the same number of total decisions, but with fewer possible outcomes at each stage. Preprocessing and post processing enables heuristic information to be included as part of the decision making process. Post processing enables the use of contextual information either available from other sources or gleaned from the actual decision making process to further process the probability factors and enhance the decisions. The use of neural net certainty measures at multiple stages of processing forces images to an abstention class, i.e. artifact. In some sense one can view this multi network approach as forcing the image data to run a gauntlet where at each stage of the gauntlet it is quite likely to be placed in an "I don't know" category. This is much more powerful than simply running through a single net because in essence what is accomplished is multiple fits of the data to templates which are much better defined than a single template could be, which allows effective use of the information. Another way to think about this is that data in different subspaces is analyzed, and is required it to fit perfectly in some sense, or well enough, with the characteristics of that subspace or else it falls out of the race. The training method of the present invention involves not simply a single pass through the training set, but selecting from a number of nets and then reducing the feature vector size. The high number of features themselves, each focusing on a particular set of physical characteristics, increases the accuracy the system.

Alternate Embodiment

Described below is an alternate embodiment of the multi-neural net imaging apparatus and method of the present invention. This alternate embodiment is similar to the basic method above, except it 1) can include a different boundary enhancement technique, 2) utilizes preprocessing based upon simple extracted particle features to screen out artifacts and mucus threads, 3) utilizes multiple neural net decision making using more complex extracted particle features, 4) utilizes post processing to analyze the ensemble of decisions, as described in more detail below. The general particle feature extraction described above is generally used, however color is not used in this alternate embodiment (images are in gray-scale). Thus, size, shape and texture are used to aid in the accurate classification of particle type.

Boundary Enhancement

The boundary enhancement described above can be used for the alternate embodiment to enhance particle feature extraction. Or, the following alternate boundary enhancement technique can be used with either embodiment to enhance particle feature extraction.

As stated above, each particle image patch typically contains an image of a particle of interest, and possibly other particles as well. This enhancement technique begins by removing the background from the actual image to produce an artificial background that is free of defects. Preferably, but not necessarily, this is performed by first taking a background image (e.g. take image of transparent fluid), and substitute for each pixel in the background image a median value that is calculated from pixel value itself and its eight (3×3) neighboring pixels. Once an entire artificial background image is formed in this manner, this background image is subtracted from the actual particle image. A standard pixel value can be added to ensure the results stay within the minimum and maximum pixel values (e.g. 0 and 255 respectively).

The image is then enlarged by a factor of at least two, preferably by utilizing a zooming algorithm as disclosed in Non-Linear Image Processing, Sanjit K. Mitra and Giovanni L. Sicuranza, Chapter 2—Part 2.4, pages 49–53, 2001, which is incorporated herein by reference. The zooming algorithm inserts rows and columns of new pixels between each of the existing rows and columns of the original pixels of an image. The new pixels are given values based on median values of the original pixels in proximity therewith. For example, in a first step, each new pixel with 4 original pixels at its diagonals is given a value of the median of those four original pixels. In a second step, each new pixel with a pair of original pixels immediately above and below, and with a pair of the new pixels on either side just given new values in the first step, is given a value of the median for those four pixels. Finally, each new pixel with a pair of original pixels immediately on either side, and with a pair of the new pixels immediately above and below just given new values in the first step, is given a value of the median for those four pixels.

A laplacian filter is then used to enhance the contrast of the patches. Other enhancement methods could be used at this time, but contrast enhancement at this point using a laplacian filter should be adequate for most applications. A morphological gradient is used next to show the particle boundaries. Morphological gradients are well known, as illustrated in "Algorithms for Image Processing and Computer Vision", J. R. Parker, Chapter 2.3, page 109, 1996, which is incorporated herein by reference, and includes subtracting a gray level dilatation from a gray level erosion for each pixel. The structuring element represents a sphere of a certain diameter around the considered pixel. The gray level dilatation includes extracting the maximum of the value of the pixels added to the value of the sphere (structuring element) for the corresponding pixel. The gray level erosion includes extracting the minimum of the value of the pixels subtracted from the value of the sphere (structuring element) for the corresponding pixel.

A threshold is then applied to the patches (i.e. identify those pixels having values that exceed a predetermined threshold) to detect the particles boundaries. Isolated and unconnected points in the patches are then eliminated by using binary morphological operators (dilation and erosion). Morphological operators are well known, as illustrated in "Algorithms for Image Processing and Computer Vision", J. R. Parker, Chapter 2, pages 69–102, 1996, which is incorporated herein by reference. A dilatation operator on a binary image includes changing the value of a pixel to 1 when all of its neighbors in the neighboring disk (structuring element) are 1. An erosion operator on a binary image consists of changing the value of all of a pixel's neighbors in the neighboring disk (structuring element) to 0. Disconnected parts of the particle boundaries are also connected through the same operation. The inside of the particles boundaries are then filled to obtain complete white blobs on black backgrounds. The largest blob in each patch is retained while the other blobs in the patch are removed. Lastly, the particle contour is smoothed using binary morphological operators (dilation and erosion). Combining dilatation and erosion operators remove peaks and fill gaps in the contour of the white blob. The resulting image is a mask image of the particle, where the white blob against the black background accurately corresponds to the size and shape of the particle of interest.

Preprocessing

Preprocessing is preferably used to screen out particles identified as artifact or as mucus threads, whereby the rest of the particles are then subjected to the full classification decision process using the neural nets described herein. While preprocessing could be based upon some of the particle features described above, the following three simple particle features are ideal for screening artifacts and mucus threads during preprocessing:

1) Size: this feature is the same as the Particle Area feature defined above, and is preferably derived from the particle mask.
2) Shape factor: this feature is defined above.
3) Contrast to background ratio (C/B ratio): A histogram of the pixels value distribution is calculated for the pixels not belonging to the particle mask (i.e. pixels belonging to the background). A 50% quantile value is extracted from that histogram, representing the "average value" of the background. The histogram of the pixels value distribution is calculated for the pixels belonging to the particle mask (i.e. belonging to the particle). A 10% quantile value is extracted from that histogram, representing how "dark" the particle is. The contrast to background ratio is calculated as the difference of the 50% quantile from the background histogram to the 10% quantile of the particle histogram, divided by the 50% quantile from the background histogram.

Figure 10:
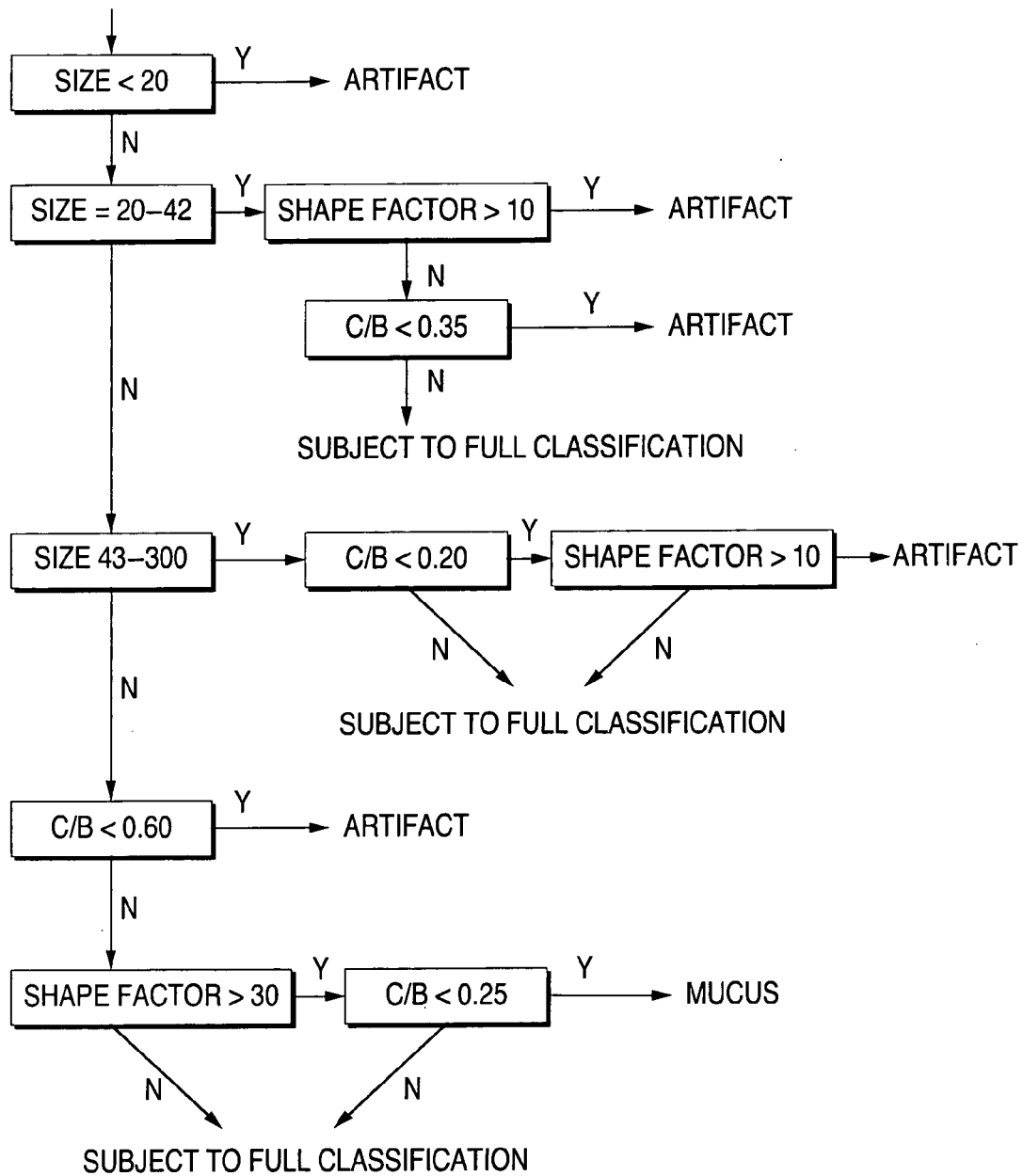
FIG. 10 is a flow diagram showing the pre-processing steps of an alternate embodiment of the present invention.

FIG. 10 illustrates an example of how artifacts and mucus strands are screened out from the full classification process. The particle sizes referred to below are the number of pixels within the area of the particle image, where the image was extracted from a field of view containing approximately 1.4 million pixels. Thus, the actual number of pixels used for each preprocessing step illustrated in FIG. 10 may vary from system to system, as the magnification of the image changes, and/or as the number of overall pixels forming the field of view changes. Once a particle is classified as an artifact or a mucus strand, pre-processing of that particle image is completed, and that particle is not subjected to the full particle classification process.

The processing of each particle image begins based upon the particle size. If the particle size is less than 20, then the particle is classified as an artifact. If the particle size is between 20–42, and either the shape factor is greater than 10 or the C/B ratio is less than 0.35, then the particle is classified as an artifact. If the particle size is between 20–42, the shape factor is not less than 10, and the C/B ratio is not less than 0.35, then the particle is to be subjected to the full classification process.

If the particle size is 43–300, the C/B ratio is less than 0.20, and the shape factor is greater than 10, then the particle is classified as an artifact. If the particle size is 43–300, but either the C/B ratio is not less than 0.20 or the shape factor is not greater than 10, then the particle is to subjected to the full classification process.

If the particle size is greater than 300, and the C/B ratio is less than 0.60, then the particle is classified as an artifact. If the particle size is greater than 300, the C/B ratio is not less than 0.60, the shaped factor is greater than 30, and the C/B ratio is less than 0.25, then the particle is classified as mucus. If the particle size is greater than 300, the C/B ratio is not less than 0.60, and either the shaped factor is not greater than 30 or the C/B ratio is not less than 0.25, then the particle is to be subjected to the full classification process.

Preprocessing can significantly reduce the computing load on the processor in several ways. First, it reduces the number of particles that are subjected to the full classification process. Second, if the particle features not involved in preprocessing are extracted and calculated after preprocessing is completed, feature extraction/calculation on those artifact and mucus particles detected during preprocessing is avoided.

Processing and Decision Making

Those particles designated during preprocessing for full classification are subjected to the multi neural net decision structures of the present invention, which classifies such particles based on probability analysis. Such classification can occur while preprocessing is on-going (for other particles), or can occur after preprocessing of all the particles is completed.

Two different examples of multi neural net decision structures are detailed above (one for the LPF scan as shown in FIG. 6B and one for the HPF scan as shown in FIG. 7B), which utilize different combinations of the 197 particle features described above. Below, an additional 11 particle features are disclosed, as well as two additional exemplary multi neural net decision structures utilizing the additional particle features to separately classify large and small particles. While any the particle features listed above and listed below can used in multi neural net decision structures, the following particle features are especially ideal for the present alternate embodiment that utilizes gray scale images of the particles. These and other particle features are preferably calculated only for particles that survive the preprocessing screening described above (i.e. not performed on artifacts and mucus strands), to reduce repetitive and needless processing and calculations.

Additional Particle Features:

1) Blob contrast: A histogram of the gray levels distribution of the pixels located inside the particle boundary is obtained (only the patch pixels that are colored in white in the mask are used). The blob contrast is defined as the difference between the Gray level of the 90% quantile and the 10% quantile, divided by the sum of these two quantiles.

2) Annulus quantiles (very useful for classification of RBC): Using binary morphological erosion, successive smaller masks of the particle surface are created. For each of these masks, the histogram of the gray level distribution of the pixels is calculated. The 50% quantile for each of these masks is obtained.

Features using the 4-neighborhood contour generated with the mask include:

3) Elongation Ratio: The contour generated is described as an ordered clock-wise or counter clock-wise suite of (x,y) coordinates from the location of each contour pixels in the patch. An iterative algorithm is applied to find a rotation transformation of the contour coordinates that result in the rectangle that contains the contour to have its biggest dimension along the X coordinate. That optimal rotation is found by successively rotating all the contour points with varying angles (from 0 to 90 degrees, by 1 degree steps). For each angle, the enclosing rectangle is found and its elongation ratio is calculated. The resulting rectangle is the one that has the highest elongation ratio value. The elongation ratio is the longest dimension of the rectangle (along X) divided by the shortest dimension of the rectangle (along Y).

4) Contour Fourier transform: The contour ordered list of coordinates is expressed as complex numbers where the real part is the x coordinate and the imaginary part is the y coordinate. A Fourier transform of that ordered list of complex numbers is calculated using a classic Direct Fourier Transform algorithm. The 5th element of that Fourier transform is used as a feature.

5) Contour Curvature Fourier Transform: From the contour ordered list of coordinates, the curvature for each contour point is calculated as the angle between the next point and the previous point in the list. Preferably the distance between these two points is ⅛th of the total number of points of the contour. A Fourier transform is calculated using a classic FFT algorithm. To express the presence of corners in the particle boundary, the feature used is the magnitude of the Fourier transform for N/4 and N/2 points, where N is the number of points of the Fourier transform.

6) Contour Curvature Average: From the contour curvature information (see above), the average of the absolute values of the curvature is calculated. Preferably, the distance between the previous and the next point of the contour for this feature is 5 points.

Features using the mask skeleton as described above include:

7) Skeleton radius: A binary morphological 1 pixel dilatation is successively applied to the skeleton extracted from the mask, until every pixel of the mask is filled. Each pixel is associated with the number of dilatation steps from the skeleton required to reach it. The distribution of the dilatation steps is the analyzed to obtain the average distance of the contour pixels to the center of the particle as represented by the skeleton.

8) Length to thickness ratio (skeleton ratio): This is the ratio of the perimeter of the mask (the number of points of the contour) to 2 times the average of the number of pixels of the two skeletons (ZSH and BZS) discussed above.

Other Features Include:

9) Headedness: The distribution of gray levels for the neighborhood of each pixels being an end-point of the skeleton is obtained. An end-point of the skeleton is a pixel that has no more than two neighbors (the calculated skeleton are 4-neighborhood types). The resulting Headedness is the difference of the maximum of these gray levels to the minimum of these gray levels, divided by the maximum gray possible (255). A preferable implementation of this feature would be to extract a histogram of pixel value distribution for each end-point neighborhood, and use the difference of some maximum and minimum quantiles).

10) Contour Concavity: From the contour ordered list of coordinates (as described above with respect to features 3 through 6), the number of points that have a negative curvature are counted. Preferably the distance between the previous point and the next point is 5 points.

11) SGF: Statistical Geometric Feature. Direct implementation of this feature is disclosed in a thesis entitled: Adaptive Multi-Scale Texture Analysis by Ross Francis Walker, University of Queensland, 1997, Pages 60–63, which is incorporated herein by reference. This method produces 48 features, only a few of which may be used.

12) Correlation to Rotation Feature. This feature calculates the correlation of the contour (as defined by its x-y coordinates) to its contour rotated by 180 degrees. A high correlation to rotation indicates a more symmetric contour.

13) First Invariant Moment: This feature is the first invariant moment of the particle defined by its contour. Invariant moments are well known, as disclosed in Digital Image Processing, R. C. Gonzalez & R. E. Woods (2nd edition), Ref., pp 514–516, 1992, which is incorporated herein by reference. The value of $\phi_1$ is calculated from the threshold image at the mean under the mask, using gray scale values instead of binary values. For a 2D continuous function f(x,y), the moment of order (p+q) is defined as $$m_{pq} = \int_{-\infty}^{\infty}\int_{-\infty}^{\infty} x^p y^q f(x,y) dx dy.$$

The central moments is expressed as $$\mu_{pq} = \int_{-\infty}^{\infty}\int_{-\infty}^{\infty} (x-\bar{x})^p (y-\bar{y})^q f(x,y) dx dy$$

where $\bar{x} = \frac{m_{10}}{m_{00}}$ and $\bar{y} = \frac{m_{01}}{m_{00}}$.

The normalized central moments are defined as $$\eta_{pq} = \frac{\mu_{pq}}{\mu_{00}^r}$$

where $$r = \frac{p+q}{2} + 1,$$

and in the present case $\mu_{00}^r$ is always 1 because $$\mu_{00} = m_{00} = 1. \{m_{00} = \int_{-\infty}^{\infty}\int_{-\infty}^{\infty} f(x,y) dx dy = 1$$

where f(x,y) is a probability}. The first invariant moment is defined as $\phi_1 = \eta_{20} + \eta_{02}$, which is invariant to translation, rotation, and scale change.

Large and Small Particle Classification

Figure 11A:
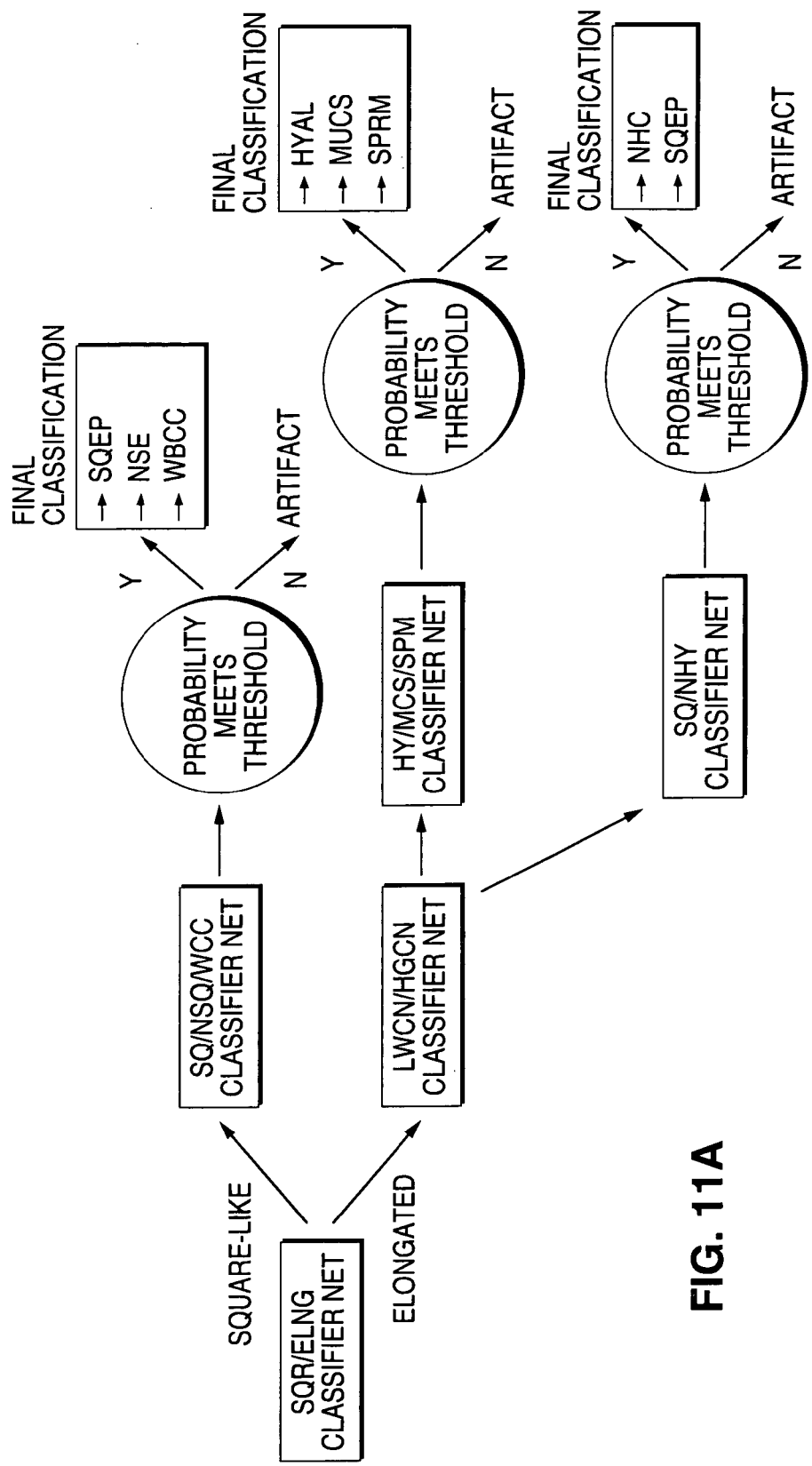
FIGS. 11A and 11B are flow diagrams showing large and small particle processing of the alternate embodiment of the present invention.
Figure 11B:
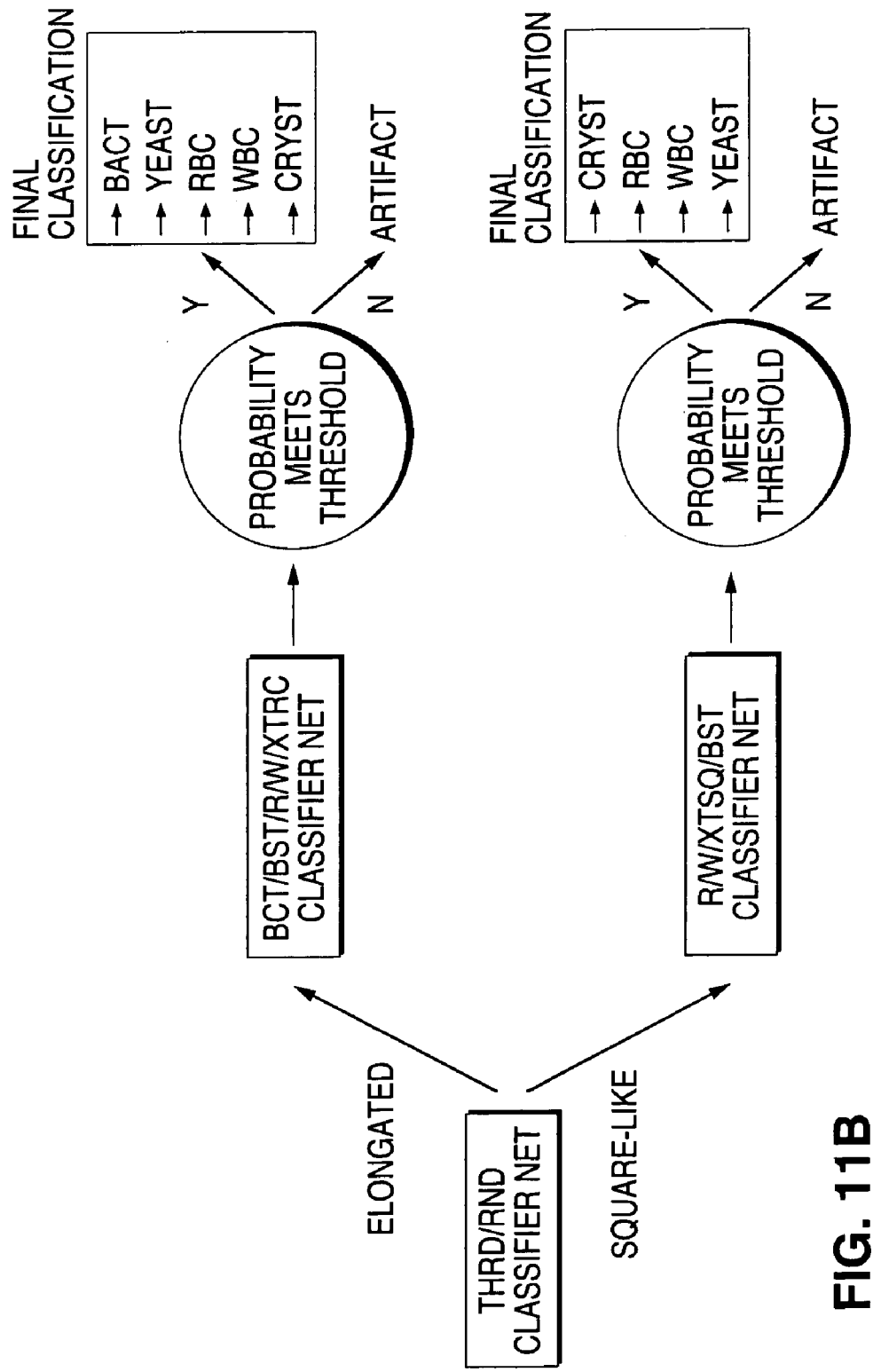

The exemplary alternate embodiment of the present invention utilizes two separate cascading multi neural net decision structures, similar to those discussed above, to classify particles: one for large particle sizes (area) (see FIG. 11A) and one for smaller particle sizes (area) (see FIG. 11B). As an example, the size threshold between small and large particle sizes is 300 pixels. Each multi neural net preferably incorporates the structure as shown and described with respect to FIG. 8. And, in each case, each neural net takes a selected subgroup of the calculated particle features discussed above, and calculates a classification probability factor ranging from zero to one that the particle meets the criteria of the net.

The large particle neural net decision structure is illustrated in FIG. 11A, and uses five neural nets to classify SQEP, NSE, WBCC, HYAL, UNCC, MUCS, and SPRM particles. The first neural net applied to the particle image is the SQR/ELNG Classifier Net, which decides whether or not the particle is elongated or more square-like. For the exemplary alternate embodiment, this net preferably includes 4 inputs (for the following particle features: shape factor, size, blob contrast, and elongation ratio), 5 neurons in the hidden layer, and two neurons in the output layer. The two outputs of this net correspond to the probabilities that the particle is or is not elongated, respectively. Whichever probability is higher constitutes the decision of the first net.

If the first net (SQR/ELNG) decides the particle is not elongated (i.e. it is square-like), a second net (SQ/NSQ/WCC) is applied to the particle image, which decides the probability that the particle is SQEP, Non Squamous Epithellal (NSE), or WBC. For the exemplary alternate embodiment, this second net preferably includes 6 inputs (for the following particle features: shape factor, size, contour curvature average, skeleton radius, skeleton ratio, and contour concavity), 5 neurons in the hidden layer, and three neurons in the output layer. The three outputs of this second net correspond to the probabilities that the particle is SQEP, Non Squamous Epithellals, and WBC, respectively. Whichever probability is the highest constitutes the decision of the second net. This decision is accepted as the final decision (and classification) for the particle, but only if the final probably meets a predetermined threshold. For the exemplary alternate embodiment, the predetermined threshold is 90%. Thus, any particle classified by this second net as SQEP, Non Squamous Epithellals, or WBC with a probability of less than 90% is given a final classification as an artifact.

If the first (SQR/ELNG) net decides the particle is elongated, a third (LWCN/HGCN) net is applied to the particle image, which decides the probability that the particle is a low contrast particle or a high contrast particle. For the exemplary alternate embodiment, this third net preferably includes 4 inputs (for the following particle features: shape factor, size, C/B ratio, and blob contrast), 5 neurons in the hidden layer, and two neurons in the output layer. The two outputs of this third net correspond to the probabilities that the particle is low contrast and high contrast, respectively. Whichever probability is the highest constitutes the decision of the third net.

If the third net (LWCN/HGCN) decides the particle is low contrast, a fourth net (HYAL/MCS/SPM) is applied to the particle image, which decides the probability that the particle is HYAL, MUCS or SPRM. For the exemplary alternate embodiment, this fourth net preferably includes 4 inputs (for the following particle features: shape factor, size, skeleton radius, and headedness), 5 neurons in the hidden layer, and three neurons in the output layer. The three outputs of this fourth net correspond to the probabilities that the particle is HYAL, MUCS and SPRM, respectively. Whichever probability is the highest constitutes the decision of the fourth net. This decision is accepted as the final decision (and classification) for the particle, so long as the finally determined probability meets the predetermined threshold (e.g. 90%). Otherwise, the particle is classified as an artifact.

If the third net (LWCN/HGCN) decides the particle is high contrast, a fifth net (SQ/NHY) is applied to the particle image, which decides the probability that the particle is a non hyaline cast (NHC) or a SQEP. For the exemplary alternate embodiment, this fifth net preferably includes 3 inputs (for the following particle features: shape factor, size, and blob contrast), 5 neurons in the hidden layer, and two neurons in the output layer. The two outputs of this fifth net correspond to the probabilities that the particle is non hyaline cast and SQEP, respectively. Whichever probability is the highest constitutes the decision of the fifth net. This decision is accepted as the final decision (and classification) for the particle, so long as the finally determined probability meets the predetermined threshold (e.g. 90%). Otherwise, the particle is classified as an artifact.

The small particle neural net decision structure is illustrated in FIG. 11B, and uses three neural nets to classify BACT, YEAST, RBC, WBC, and CRYST. The first neural net applied to the particle image is the THRD/RND net, which decides whether or not the particle is elongated or more square-like. For the exemplary alternate embodiment, this net preferably includes 3 inputs (for the following particle features: shape factor, size, and elongation ratio), 5 neurons in the hidden layer, and two neurons in the output layer. The two outputs of this net correspond to the probabilities that the particle is or is not elongated, respectively. Whichever probability is higher constitutes the decision of the first net.

If the first net (THRD/RND) decides the particle is elongated, a second net (BCT/BST/R/W/XTRC) is applied to the particle image, which decides the probability that the particle is BACT, YEAST, RBC, WBC or CRYST. For the exemplary alternate embodiment, this second net preferably includes 9 inputs (for the following particle features: shape factor, size, C/B ratio, contour Fourier transform, contour curvature Fourier transform (twice used), Correlation to Rotation, skeleton radius, and First Invariant Moment, 10 neurons in the hidden layer, and five neurons in the output layer. The five outputs of this second net correspond to the probabilities that the particle is BACT, YEAST, RBC, WBC and CRYST, respectively. Whichever probability is the highest constitutes the decision of the second net. This decision is accepted as the final decision (and classification) for the particle, but only if the final probably meets the predetermined threshold (e.g. 90%). Otherwise, the particle is classified as an artifact.

If the first net (THRD/RND) decides the particle is not elongated (i.e. more square-like), a third net (R/W/XTSQ/BST) is applied to the particle image, which decides the probability that the particle is CRYST, RBC, WBC or YEAST. For the exemplary alternate embodiment, this second net preferably includes 10 inputs (for the following particle features: shape factor, size, blob contrast, contour Fourier transform, contour curvature Fourier transform (twice used), annulus quantiles (thrice used), and contour concavity), 10 neurons in the hidden layer, and four neurons in the output layer. The four outputs of this third net correspond to the probabilities that the particle is CRYST, RBC, WBC and YEAST, respectively. Whichever probability is the highest constitutes the decision of the third net. This decision is accepted as the final decision (and classification) for the particle, but only if the final probably meets the predetermined threshold (e.g. 90%). Otherwise, the particle is classified as an artifact.

Both the large and small particle neural net structures described above use upper layer neural net(s) to decide which lower level neural net(s) should be used for final particle classification, and the lower level neural net(s) produce a probability factor that is accepted as the final particle classification, preferably only if the final probability decision meets the predetermine threshold (e.g. 90%) of certainty.

It should be noted that the particle features used by the neural net structures could be all calculated up front, before the neural nets are employed, or can be calculated during neural net processing on an as needed basis. The training of the above described neural nets for the alternate embodiment is preferably performed using the same methodology as described above.

Post-Processing Decision Making

As stated above, once all the particle images are classified by particle type, post decision processing is preferably performed to further increase the accuracy of the classification results. This processing considers the complete set of results, and removes classification results that as a whole are not considered trustworthy.

Figure 12:
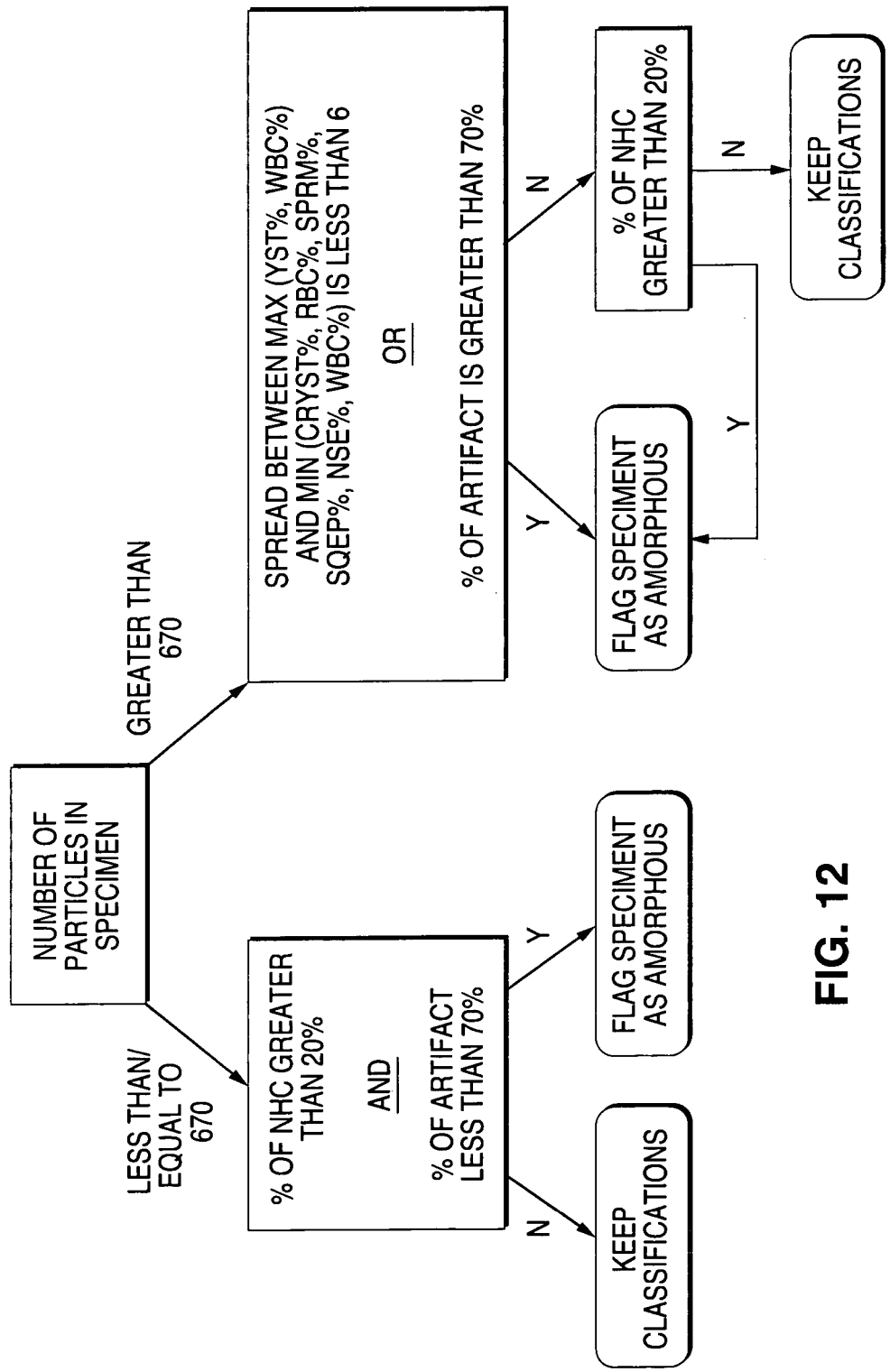
FIG. 12 is a flow diagram showing the post processing steps of the alternate embodiment of the present invention.

In addition to the post-processing criteria listed above, other post processing can alternately or additionally be performed with the alternate embodiment of the present invention. One example of such post-processing is illustrated in FIG. 12. Using the results of the classifications, heuristical analysis is performed on the distribution of the type of particles recognized in the specimen, to determine the presence of amorphous elements in quantity enough for the entire specimen to be reclassified or flagged as "amorphous". Such a reclassified or flagged specimen should then be manually reviewed by a skilled operator to verify the proper classifications of the particle therein.

As illustrated in FIG. 12, for a low number of particles (e.g. below 670), the specimen is reclassified or flagged Amorphous if the percentage of NHC is above a threshold (e.g. 20%) and the percentage of Artifact is below a threshold (e.g. 70%). For a high number of particles (e.g. above 670), the specimen is reclassified or flagged Amorphous if the maximum spread of percentages of specific classes of particles is below a threshold (e.g. 6%), or if the percentage of Artifact is above a threshold (e.g. 70%), or the percentage of Artifact is below a threshold (e.g. 70%) and the percentage of NHC is above a threshold (e.g. 20%).

It is to be understood that the present invention is not limited to the embodiments described above and illustrated herein. Therefore, it should be understood that while the present invention is described with respect to the classification of images of biological samples, it also includes image analysis for any image having features that can be extracted and used to classify the image. For example, the present invention can be used for facial recognition. Features can be extracted to identify and classify the shape, size, location and dimension of the eyes, nose, mouth, etc., or more general features such as face shape and size, so that the facial images can be identified and classified into predetermined classifications.

What is claimed is:

1. A method of classifying a plurality of elements in images, the method comprising:
    forming electronic images of a field of view containing elements, wherein each of the elements has a plurality of features;
    extracting and processing a first subgroup of the plurality of features from the images of the plurality of elements to segregate the plurality of elements into first and second groups; and
    determining a classification class only for each of the elements in the first group by selecting and processing a second subgroup of the extracted features to determine a physical characteristic of the element, and selecting and processing a third subgroup of the extracted features in response to the determined physical characteristic to determine a classification class of the element,
    wherein the second group of elements bypasses the determination of classification class.

2. The method of claim 1, wherein the elements are biological particles that include artifacts and mucus, and wherein the extracting and processing of the first features subgroup segregates the artifacts and the mucus into the second group of elements.

3. The method of claim 1, wherein the elements are biological particles, and wherein the extracting and processing of the first features subgroup further comprises:
    segregating any of the elements having a size below a first threshold into the second group of elements as artifacts;
    segregating any of the elements having a size above the first threshold and below a second threshold, and having a roundness below a roundness threshold or a darkness relative to a background below a darkness threshold, into the second group of elements as artifacts;
    segregating any of the elements having a size above the second threshold, and having a darkness relative to a background below a darkness threshold, into the second group of elements as artifacts; and
    segregating any of the elements having a size above the second threshold, and having a roundness greater than a roundness threshold and a darkness relative to a background below a darkness threshold, into the second group of elements as mucus.

4. The method of claim 1, further comprising:
    modifying the determined classification class of at least some of the elements of the first group based upon the determined classification class determinations for all the elements in the first group.

5. The method of claim 1, wherein the processings of the second subgroup of the extracted features are performed by a first neural net, and wherein the processings of the third subgroup of the extracted features are each performed by one of a plurality of neural nets.

6. The method of claim 5, wherein for each of the elements in the first group:
    the first neural net dictates which one of the plurality of neural nets processes the third subgroup of the extracted features.

7. The method of claim 6, wherein:
    the second subgroup of the extracted features includes: element roundness and element size; and
    the third subgroup of the extracted features includes: element size.

8. The method of claim 7, wherein:
    the second subgroup of the extracted features further includes: an elongation ratio.

9. The method of claim 7, wherein:
    the second subgroup of the extracted features further includes: element contrast against an element background.

10. The method of claim 7, wherein:
    the second subgroup of the extracted features further includes: an element gray level distribution.

11. The method of claim 1, further comprising:
    segregating the first group of elements into a third group of the elements having a size below a predetermined size threshold, and into a fourth group of the elements having a size above the predetermined size threshold, and wherein the determining of the classification class is performed using a first network of neural nets for the third group of the elements and using a second network of neural nets different from the first network of neural nets for the fourth group of the elements.

12. The method of claim 1, wherein the physical characteristic is a predetermined amount of element elongation, and for each of the elements in the first group, the determined classification class is selected from one or more groups comprising bacteria, yeast, red blood cells, white blood cells, and crystals.

13. The method of claim 1, wherein the physical characteristic is a predetermined amount of contrast, and the determined classification class is selected from one or more groups comprising HYAL, MUCS, SPRM, NHC and SQEP.

14. The method of claim 1, wherein each of the electronic images is formed of rows and columns of original pixels each having a pixel value, and wherein the forming of each one of the electronic images further comprises:
    inserting rows and columns of new pixels among the rows and columns of the original pixels; and
    giving a pixel value to each of the new pixels based upon the pixel values of the original pixels in proximity therewith.

15. The method of claim 1, wherein each of the determinations includes assigning a probability factor, and further including modifying the determined classification class to an artifact classification in the event one or more of the probability factors used to classify the element fails to exceed a predetermined threshold value.

16. An apparatus for classifying a plurality of elements in images, the method comprising:
    an imaging system for forming electronic images of a field of view containing elements, wherein each of the elements has a plurality of features;
    at least one processor for:
        extracting and processing a first subgroup of the plurality of features from the images of the plurality of elements to segregate the plurality of elements into first and second groups; and
        determining a classification class only for each of the elements in the first group by selecting and processing a second subgroup of the extracted features to determine a physical characteristic of the element, and selecting and processing a third subgroup of the extracted features in response to the determined physical characteristic to determine a classification class of the element, wherein the second group of elements bypasses the determination of classification class.

17. The apparatus of claim 16, wherein the elements are biological particles that include artifacts and mucus, and wherein the extracting and processing of the first features subgroup by the at least one processor segregates the artifacts and the mucus into the second group of elements.

18. The apparatus of claim 16, wherein the elements are biological particles, and wherein the extracting and processing of the first features subgroup by the at least one processor further comprises:

segregating any of the elements having a size below a first threshold into the second group of elements as artifacts;

segregating any of the elements having a size above the first threshold and below a second threshold, and having a roundness below a roundness threshold or a darkness relative to a background below a darkness threshold, into the second group of elements as artifacts;

segregating any of the elements having a size above the second threshold, and having a darkness relative to a background below a darkness threshold, into the second group of elements as artifacts; and segregating any of the elements having a size above the second threshold, and having a roundness greater than a roundness threshold and a darkness relative to a background below a darkness threshold, into the second group of elements as mucus.

19. The apparatus of claim 16, wherein the at least one processor modifies the determined classification class of at least some of the elements of the first group based upon the determined classification class determinations for all the elements in the first group.

20. The apparatus of claim 16, wherein the at least one processor utilizes a first neural net for the processings of the second subgroup of the extracted features, and utilizes one of a plurality of neural nets for each of the processings of the third subgroup of the extracted features.

21. The apparatus of claim 20, wherein for each of the elements in the first group:

the first neural net dictates which one of the plurality of neural nets is utilized to process the third subgroup of the extracted features.

22. The apparatus of claim 21, wherein:

the second subgroup of the extracted features includes: element roundness and element size; and the third subgroup of the extracted features includes: element size.

23. The apparatus of claim 22, wherein:

the second subgroup of the extracted features further includes: an elongation ratio.

24. The apparatus of claim 22, wherein:

the second subgroup of the extracted features further includes: element contrast against an element background.

25. The apparatus of claim 22, wherein:

the second subgroup of the extracted features further includes: an element gray level distribution.

26. The apparatus of claim 16, wherein the at least one processor segregates the first group of elements into a third group of the elements having a size below a predetermined size threshold, and into a fourth group of the elements having a size above the predetermined size threshold, and wherein the at least one processor determines the classification class by utilizing a first network of neural nets for the third group of the elements and using a second network of neural nets different from the first network of neural nets for the fourth group of the elements.

27. The apparatus of claim 16, wherein the physical characteristic is a predetermined amount of element elongation, and for each of the elements in the first group, the determined classification class is selected by the at least one processor from one or more groups comprising bacteria, yeast, red blood cells, white blood cells, and crystals.

28. The apparatus of claim 16, wherein the physical characteristic is a predetermined amount of contrast, and the determined classification class is selected by the at least one processor from one or more groups comprising HYAL, MUCS, SPRM, NHC and SQEP.

29. The apparatus of claim 16, wherein each of the electronic images is formed of rows and columns of original pixels each having a pixel value, and wherein the at least one processor inserts rows and columns of new pixels among the rows and columns of the original pixels, and gives a pixel value to each of the new pixels based upon the pixel values of the original pixels in proximity therewith.

30. The apparatus of claim 16, wherein each of the determinations by the at least one processor includes assigning a probability factor, and wherein the at least one processor modifies the determined classification class to an artifact classification in the event one or more of the probability factors used to classify the element fails to exceed a predetermined threshold value.

* * * * *